US012178867B2

(12) United States Patent
Philip

(10) Patent No.: US 12,178,867 B2
(45) Date of Patent: Dec. 31, 2024

(54) MHC CLASS I ASSOCIATED PEPTIDES FOR PREVENTION AND TREATMENT OF MULTIPLE FLAVI VIRUS

(71) Applicant: Emergex Vaccines Holding Limited, Oxfordshire (GB)

(72) Inventor: Ramila Philip, Sparks, NV (US)

(73) Assignee: Emergex Vaccines Holding Limited, Oxfordshire (GB)

( * ) Notice: Subject to any disclaimer, the term of this patent is extended or adjusted under 35 U.S.C. 154(b) by 0 days.

(21) Appl. No.: 18/332,022

(22) Filed: Jun. 9, 2023

(65) Prior Publication Data

US 2023/0346908 A1 Nov. 2, 2023

Related U.S. Application Data

(63) Continuation of application No. 16/957,931, filed as application No. PCT/GB2019/050024 on Jan. 4, 2019, now Pat. No. 11,690,904.

(60) Provisional application No. 62/614,375, filed on Jan. 6, 2018.

(51) Int. Cl.

| | |
|---|---|
| ***A61K 47/00*** | (2006.01) |
| ***A61K 39/12*** | (2006.01) |
| ***A61K 47/69*** | (2017.01) |
| *A61K 39/00* | (2006.01) |

(52) U.S. Cl.
CPC .......... *A61K 39/12* (2013.01); *A61K 47/6929* (2017.08); *A61K 2039/60* (2013.01)

(58) Field of Classification Search
None
See application file for complete search history.

(56) References Cited

U.S. PATENT DOCUMENTS

| | | | | |
|---|---|---|---|---|
| 8,512,991 | B2 * | 8/2013 | Qasba | C12P 21/005 424/94.5 |
| 8,568,781 | B2 | 10/2013 | Rademacher et al. | |
| 9,079,765 | B2 | 7/2015 | Himmler et al. | |
| 9,637,521 | B2 | 5/2017 | Philip | |
| 10,124,055 | B2 | 11/2018 | Ciaramella et al. | |
| 2015/0110825 | A1 * | 4/2015 | Sasisekharan | A61K 39/155 435/348 |
| 2016/0050754 | A1 | 2/2016 | Bekke | |

FOREIGN PATENT DOCUMENTS

| | | | | |
|---|---|---|---|---|
| WO | 0232404 | A2 | 4/2002 | |
| WO | 2005014627 | A1 | 2/2005 | |
| WO | 2006037979 | A2 | 4/2006 | |
| WO | 2007015105 | A2 | 2/2007 | |
| WO | 2007122388 | A2 | 11/2007 | |
| WO | WO 2011/084604 | A2 | 7/2011 | |
| WO | WO2013/003579 | * | 1/2013 | A61K 39/12 |
| WO | WO 2013/003579 | A1 | 1/2013 | |
| WO | 2013059403 | A1 | 4/2013 | |
| WO | WO 2015/175361 | A1 | 11/2015 | |
| WO | WO 2016181147 | | 11/2016 | |
| WO | 2017015463 | | 1/2017 | |
| WO | 2017140905 | A1 | 8/2017 | |
| WO | 2018218355 | A1 | 12/2018 | |
| WO | 2019058133 | A2 | 3/2019 | |
| WO | 2019092142 | A1 | 5/2019 | |
| WO | 2019186199 | A1 | 10/2019 | |

OTHER PUBLICATIONS

Niikura et al. (ACSNANO, 2013, p. 3926-3938).*

Calvet et al., Detection and sequencing of Zika virus from amniotic fluid of fetuses with microcephaly in Brazil: a case study. the Lancet Infectious diseases. 2016;16(6):653-60.

Chavant et al., The Pregvaxgrip study: a cohort study to assess foetal and neonatal consequences of in utero exposure to vaccination against A(HINI)v2009 influenza. Drug safety. 2013;36(6):455-65.

Cheepsattayakom A CR. Zika Virus Infection and Disease. J Hum Virol & Retrovirol 2016;3(2):82.

Comber et al., MHC Class I Presented T Cell Epitopes as Potential Antigens for Therapeutic Vaccine against HBV Chronic Infection. Hepatitis research and treatment. 2014;2014:860562.

Comber Joseph D et al., “Dengue virus specific dual HLA binding T cell epitopes induce CD8(+) T cell responses in seropositive individuals”, Human Vaccines and Immunotherapeutics, Taylor & Francis, US, vol. 10, No. 12, 2014, pp. 3531-3543.

Conlin et al., Safety of the pandemic H1N1 influenza vaccine among pregnant U.S. military women and their newborns. Obstetrics and gynecology. 2013;121(3):511-8.

Dar Hamza et al., “Prediction of promiscuous T-cell epitopes in the Zika virus polyprotein: Anin silicoapproach”, Asian Pacific Journal of Tropical Medicine, Hainan Medical College, Singapore, vol. 9, No. 9, 2016, pp. 844-850.

Elong Ngono Annie et al., “Mapping and Role of the CD8+T Cell Response During Primary Zika Virus Infection in Mice”, Cell Host & Microbe, Elsevier, NL, vol. 21, No. 1, 2017, pp. 35-46.

Ghatak et al. (Accession No. QEV86434.1, Aug. 2019).

Hamel et al., Biology of Zika Virus Infection in Human Skin Cells. Journal of virology. 2015;89(17):8880-96.

Hermann et al., Human fetuses are able to mount an adultlike CDS T-cell response. Blood. 2002; 100(6):2153-8.

Huang X. et al, “A novel immunization approach for dengue infection based on conserved T cell epitopes formulated in calcium phosphate nanoparticles” Hum Vaccin Immunother, Sep. 21, 2017, vol. 13, No. 11, pp. 2612-2625.

Huarong Huang et al., “CD8(+) T Cell Immune Response in immuncompetent Mice during Zika Virus Infection”, Journal of Virology., vol. 91, No. 22, 2017, pp. e00900-17.

Hunt et al., HLA-G and immune tolerance in pregnancy. FASEB journal : official publication of the Federation of American Societies for Experimental Biology. 2005;19(7):681-93.

Jinsheng Wen et al., “Identification of Zika virus epitopes reveals immunodominant and protective roles for dengue virus cross-reactive CD8+ T cells”, Nature Microbiology, vol. 2, 2017, p. 17036.

(Continued)

*Primary Examiner* — Agnieszka Boesen
(74) *Attorney, Agent, or Firm* — Melissa L. Sistrunk

(57) ABSTRACT

The invention provides a vaccine composition comprising a flavi peptide comprising one or more CD8+ T cell epitopes.

20 Claims, 6 Drawing Sheets

Specification includes a Sequence Listing.

(56) References Cited

OTHER PUBLICATIONS

Kaposy et al., Overcoming liability concerns in vaccine trials involving pregnant women. Accountability in research. 2012;19(3):156-74.
Khan et al., Conservation and variability of dengue virus proteins: implications for vaccine design. PLoS neglected tropical diseases. 2008;2(8):e272.
Le Bouteiller P. HLA-G in human early pregnancy: control of uterine immune cell activation and likely vascular remodeling. Biomedical journal. 2015;38(I):32-8.
Marchant et al., Mature CD8(+) T lymphocyte response to viral infection during fetal life. The Journal of clinical Investigation. 2003;111(11):1747-55.
Meaney-Delman et al., Zika Virus and Pregnancy: What Obstetric Health Care Providers Need to Know. Obstetrics and gynecology. 2016;127(4):642-8.
Meziere et al., (1997) J. Immunol. 159, 3230-3237.
Mold et al., Maternal alloantigens promote the development of tolerogenic fetal regulatory T cells in utero. Science. 2008;322(5907): 1562-5.
Rasmussen et al., Zika Virus and Birth Defects-Reviewing the Evidence for Causality. the New England journal of medicine. 2016;374(20):1981-7.
Rastogi et al., Antigen-specific immune responses to influenza vaccine in utero. the Journal of clinical investigation. 2007;117(6):1637-46.
Rothman AL. Dengue: defining protective versus pathologic immunity. the Journal of clinical investigation. 2004;113(7):946-51.
Tao Wenqian et al., "Gold nanoparticle-M2e conjugate coformulated with CpG induces protective immunity against Influenza A virus", Nanomedicine, Future Medicine Ltd., London, GB, vol. 9, No. 2 Feb. 1, 2014 (Feb. 1, 2014), pp. 237-252.
Testa et al., Conserved MHC class I-presented dengue virus epitopes identified by immunoproteomics analysis are targets for cross-serotype reactive T-cell response. J Infect Dis. 2012;205(4):647-55.
Testa et al., MHC class I-presented T cell epitopes identified by immunoproteomics analysis are targets for a cross reactive influenza-specific T cell response. PLoS One. 2012;7(1 I):e48484.
Vanderbeeken et al., In utero immunization of the fetus to tetanus by maternal vaccination during pregnancy. American journal of reproductive immunology and microbiology : AJRIM. 1985;8(2):39-42.
Weiskopf et al., T-cell immunity to infection with dengue virus in humans. Frontiers in immunology. 2014;5:93.
Wen J. et al, "Identification of Zika virus epitopes reveals immunodominant and protective roles for dengue virus cross-reactive CD8+ T cells", Nat Microbiol., Mar. 13, 2017, vol. 2, pp. 17036.
Le Bouteiller P. HLA-G in human early pregnancy: control of uterine immune cell activation and likely vascular remodeling. Biomedical journal. 2015;38(1):32-8.
Testa et al., MHC class I-presented T cell epitopes identified by immunoproteomics analysis are targets for a cross reactive influenza-specific T cell response. PLoS One. 2012;7(1 1):e48484.
Office Action issued on Jun. 6, 2023 by the EPO in the corresponding Patent Application No. 19 701 899.7-1111.
Examination report No. 2 issued in corresponding Australian Patent Application No. 2019205627 dated Jan. 9, 2024.
Wu et al, "Galactosylated LDL nanoparticles: a novel targeting delivery system to deliver antigen to macrophages and enhance antigen specific T cell responses.", *Molecular pharmaceutics*, 2009, 6 (5): 1506-1517.
Huang et al, "A novel immunization approach for dengue infection based on conserved T cell epitopes formulated in calcium phosphate nanoparticles", *Human vaccines & immunotherapeutics*, 2017; 13(11): 2612-2625.
Phanse et al., "A systems approach to designing next generation vaccines: combining α-galactose modified antigens with nanoparticle platforms", *Scientific reports*, 2014, 4:3775.
Wang et al., "Application of galactose-modified liposomes as a potent antigen presenting cell targeted carrier for intranasal immunization.", *Acta biomaterialia*, 2013, 9:5681-5688.
Wendorf et al., "A practical approach to the use of nanoparticles for vaccine delivery.", *Journal of pharmaceutical sciences*, 2006, 95(12):2738-2750.

* cited by examiner

Genome organisation of the flavivirus

| 5'NC | C | PrM/M | E | NS1 | NS2A/B | NS3 | NS4A/B | NS5 | 3'NC |

MHC CLASS I ASSOCIATED PEPTIDES FOR PREVENTION AND TREATMENT OF MULTIPLE FLAVI VIRUS

CROSS-REFERENCE TO RELATED APPLICATIONS

This application is a continuation of U.S. Non-Provisional application Ser. No. 16/957,931 filed Jun. 25, 2020, which is a national phase application under 35 U.S.C. § 371 that claims priority to International Application No. PCT/GB2019/050024 filed Jan. 4, 2019, which claims priority to U.S. Provisional Application No. 62/614,375 filed Jan. 6, 2018, all of which are incorporated herein by reference in their entirety.

INCORPORATION OF SEQUENCE LISTING

The instant application contains a Sequence Listing, named "MEWB_P0004US_C1_SL.XML" (22,545 bytes; created Jun. 8, 2023) which has been submitted electronically in XML format and is hereby incorporated by reference in its entirety.

FIELD OF THE INVENTION

The invention relates to vaccine compositions comprising flavivirus peptides, and the use of such compositions for the treatment and prevention of flavivirus infection.

BACKGROUND TO THE INVENTION

Flaviviruses are a family of positive sense, single stranded, enveloped RNA viruses that may infect humans and pose a significant threat to public health. In particular, flaviviruses are the causative agent of Zika fever, Dengue fever, Japanese encephalitis, yellow fever and West Nile fever. These diseases are commonly characterised by symptoms that include fever, vomiting, headache, joint pain and muscle pain, though each disease may also be associated with more serious symptoms. For instance, mother-to-child transmission of Zika virus during pregnancy can cause brain malformations, and Zika virus infection has also been linked to Guillain-Barré syndrome. Dengue fever may progress into life-threatening Dengue haemorrhagic syndrome or Dengue shock syndrome. Yellow fever may induce liver damage, which may result in bleeding and kidney problems. West Nile fever may spread to the nervous system, causing encephalitis or meningitis.

Flaviviruses are arboviruses, meaning that they are transmitted by infected arthropod vectors such as mosquitos and ticks. The geographical distribution of flaviviruses is primarily determined by that of their arthropod vector. For the most part, the vectors are confined to tropical and subtropical regions, such as Southeast Asia and South America. However, climate change appears to be broadening the distribution of some vectors, thereby increasing the population at risk of contracting flavivirus infections. Furthermore, the mosquito responsible for spreading Zika virus and yellow fever virus has been shown to be able to adapt to survive in high-density urban areas. It is therefore important to find effective methods for containing flavivirus infection. While some flaviviruses (such as West Nile virus) only incidentally infect humans, other flaviviruses (such as yellow fever virus, Dengue virus and Zika virus) exist predominantly in an arthropod-human life cycle. Such flaviviruses grow well in the human host, and high viral titres allow infection to cycle back to arthropod vectors and onto new human hosts. In either case, vector-born transmission and the ability to infect other species such as monkeys and birds means that flavivirus infections tend to spread quickly and easily. Controlling the spread of flavivirus infections is therefore challenging.

The structure of the flavivirus genome also contributes to the challenge of controlling spread. Few proof-reading and correction mechanisms exist for the replication of single-stranded RNA. Therefore, mutations arising in the course of replication frequently remain in the genome and are passed to the next generation. Flaviviruses therefore evolve quickly.

While a safe and effective vaccine exists for yellow fever virus infection and for Japanese encephalitis virus infection, this is not the case for Zika virus, Dengue virus or West Nile virus infection. A vaccine for Dengue virus exists, but is recommended only for use in individuals who have previously had a Dengue virus infection, as outcomes may be worsened in those who have not previously been infected. Being exposed to one serotype of Dengue virus (such as DENV-1, DENV-2, DENV-3 or DENV-4) potentially worsens subsequent infections with another Dengue serotype. As Zika virus is closely related to Dengue virus, any Zika virus vaccine also needs to minimize the possibility of antibody-dependent enhancement of Dengue virus infection. There is therefore a need for effective vaccines against Zika virus, Dengue virus, and West Nile virus infection.

SUMMARY OF THE INVENTION

The present invention relates to a flavivirus vaccine composition that stimulates an immune response while avoiding the adverse clinical effects often associated with vaccines containing viruses. The vaccine composition may provide protection against multiple species of flavivirus (e.g. Zika virus, Dengue virus, West Nile virus, yellow fever virus, and/or Japanese encephalitis virus) and/or multiple lineages or serotypes of a particular species (e.g. African Zika virus, Asian Zika virus, DENV-1, DENV-2, DENV-3 and/or DENV-4).

The present inventors have surprisingly identified that a nanoparticle, for example a gold nanoparticle, may be used to induce an efficient response to a vaccine composition designed to stimulate a T cell response against a flavivirus. Use of a nanoparticle abrogates the need to use a virus in the vaccine composition. The use of a traditional adjuvant, which may be associated with adverse reactions in the clinic, is also avoided.

Therefore, the likelihood of an individual experiencing an adverse reaction following administration of the vaccine composition is reduced.

The present inventors have also identified number of peptides that are conserved between different flaviviruses and are presented by MHC molecules on cells infected with those viruses. Inclusion of such conserved peptides in the vaccine composition may confer protective capability against multiple species of flavivirus and/or multiple lineages or serotypes of a particular species. Including multiple conserved peptides that bind to different HLA supertypes in the vaccine composition results in a vaccine that is effective in individuals having different HLA types.

Accordingly, the present invention provides a vaccine composition comprising a flavivirus peptide comprising one or more of the CD8+ T cell epitopes set out in SEQ ID NOs: 1 to 23 or a variant thereof. In some aspects, the flavivirus peptide may be attached to a nanoparticle.

The present invention further provides:

- a vaccine composition comprising a polynucleotide encoding a flavivirus peptide comprising one or more of the CD8+ T cell epitopes set out in SEQ ID NOs: 1 to 23 or a variant thereof;
- a method of preventing or treating a flavivirus infection, comprising administering the vaccine composition of any one of the preceding claims to an individual infected with, or at risk of being infected with, a flavivirus;
- a vaccine composition of the invention for use in a method of preventing or treating a flavivirus infection in an individual;
- an ex vivo method for generating cytotoxic T lymphocytes (CTLs) for use in passive immunotherapy, comprising contacting T cells obtained from a subject infected with a flavivirus with a flavivirus peptide comprising one or more of the CD8+ T cell epitopes set out in SEQ ID NOs: 1 to 23 or a variant thereof; and
- a method for diagnosing a flavivirus infection in a subject, comprising (i) contacting T cells obtained from the subject with a flavivirus peptide comprising one or more of the CD8+ T cell epitopes set out in SEQ ID NOs: 1 to 23 or a variant thereof and (ii) determinging the response of the T cells to the flavivirus peptide.

BRIEF DESCRIPTION OF THE FIGURES

(FIG. 1A) Dengue, Zika and Chikungunya viruses are all carried by the same mosquito and there is considerable clinical overlap between the three. (FIG. 1B) There is also considerable clinical overlap between Zika, Dengue, Yellow fever, Japanese encephalitis virus and over 66 other flaviviruses.

(FIG. 3A) Utilizing a healthy (naive) human HLA-A2+ donor, peripheral blood mononuclear cells (PBMCs) were stimulated with peptide epitopes in a cytokine cocktail to induce antigen specific CTL response. These stimulated PBMCs were then assayed by co-culturing peptide loaded targets for antigen specific response. TAP-deficient cells (T2) were used for peptide loading, and blank T2 cells used as control. Expanded PBMCs were assayed for both CD107a degranulation and interferon gamma (IFN-g) markers by flow cytometry. All 6 peptide epitopes induced CD8+ CD107a and IFNg expression to peptide loaded T2 cells in a peptide specific manner. Peptide "PMA" has a particular pronounced IFNg+ effect. (FIG. 3B) Utilizing a healthy (naive) human HLA-A2+ donor, peripheral blood mononuclear cells (PBMCs) were stimulated with peptide epitopes in a cytokine cocktail to induce antigen specific CTL response. These stimulated PBMCs were then assayed by co-culturing with Hep2G infected cells (DV2/Zika). Uninfected HepG2 cells were used as control. Expanded PBMCs were assayed for both CD107a degranulation and interferon gamma (IFN-g) markers by flow cytometry.

FIG. 5 shows that HepG2 target cells contain peptide class I targets that are able to simulate spleen cells from transgenic A2 mice. Acid stripping of the peptides makes the cells non-response.

FIG. 6 shows that spleen cells from unimmunized mice do not respond to dengue or zika infected cells. In contrast A2 mice immunized with NP-Dengue or NP-Zika peptides are able to kill both Dengue or Zika infected HepG2 cells.

DETAILED DESCRIPTION OF THE INVENTION

Vaccine Compositions

Figure 1A:
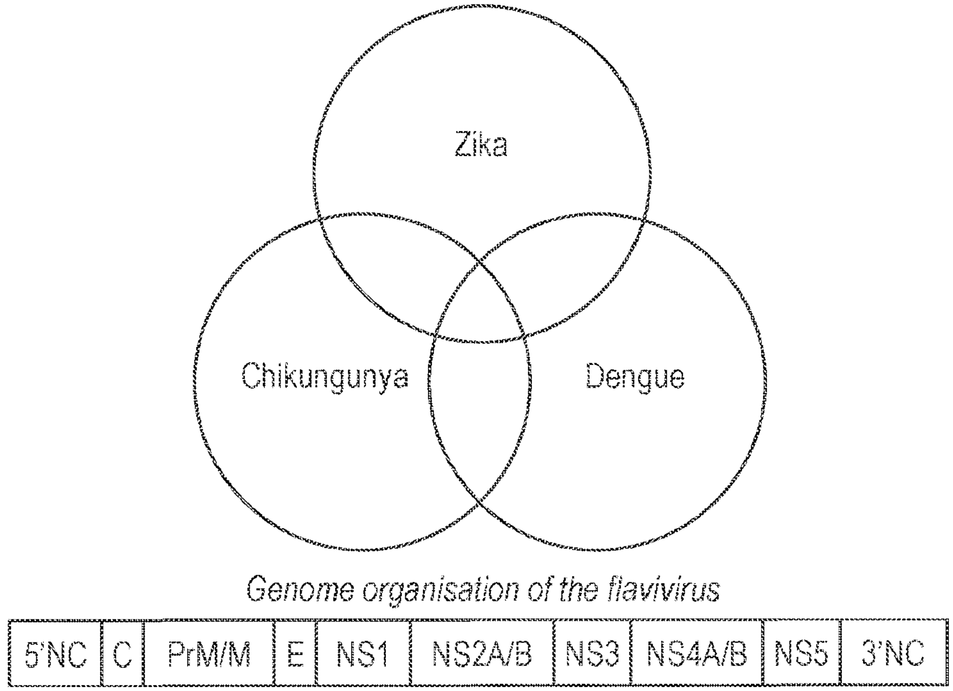
FIGS. 1A and 1B.
Figure 1B:
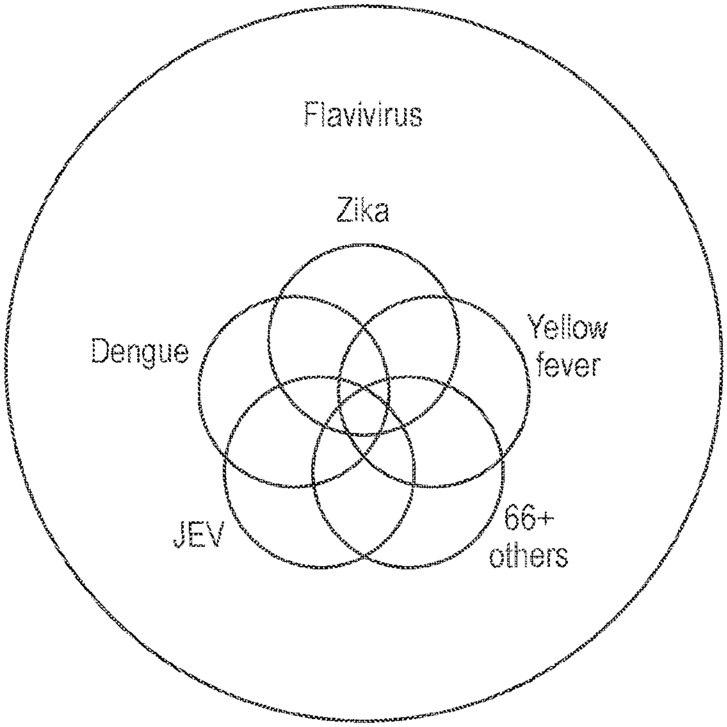

The present invention provides a vaccine composition comprising a flavivirus peptide comprising one or more of the CD8+ T cell epitopes set out in SEQ ID NOs: 1 to 23 or a variant thereof. The present invention provides a vaccine composition comprising a polynucleotide encoding a flavivirus peptide comprising one or more of the CD8+ T cell epitopes set out in SEQ ID NOs: 1 to 23 or a variant thereof. These vaccine compositions have a number of benefits which will become apparent from the discussion below. The key benefits are though summarised here.

Firstly, the vaccine composition of the invention advantageously comprises (i) a flavivirus peptide comprising one or more of the CD8+ T cell epitopes set out in SEQ ID NOs: 1 to 23 and newly identified by the inventors, or a variant thereof; or (ii) a polynucleotide a flavivirus peptide comprising one or more of the CD8+ T cell epitopes set out in SEQ ID NOs: 1 to 23 or a variant thereof. As demonstrated in the Examples, the vaccine composition is therefore capable of stimulating a cellular immune response (e.g. a CD8+ T cell response) against a flavivirus. CD8+ cytotoxic T lymphocytes (CTLs) mediate viral clearance via their cytotoxic activity against infected cells. Stimulating cellular immunity may therefore provide a beneficial defence against flavivirus infection.

Secondly, a number of the CD8+ T cell epitopes identified by the present inventors may be conserved between many different flaviviruses, and may be presented by MHC molecules on cells infected with those viruses. For instance, the present inventors have identified that certain CD8+ T cell epitopes expressed in cells infected with Dengue virus are 100% homologous with peptides expressed by other flaviviruses, such as Zika virus, or other related viruses such as the alphavirus Chikungunya virus (see Table 1). Inclusion of such conserved peptides in the vaccine composition may confer protective capability against (i) related types of virus, (ii) multiple species of flavivirus and/or (iii) multiple lineages or serotypes of a particular species, i.e. confer cross-protection. 100% homology between viruses is not required for cross-protection to be conferred. Rather, cross-protection may arise following immunisation with a sequence that is, for example, about 50% or more (such as 60%, 70%, 75%, 80%, 90%, 95%, 98% or 99%) homologous to a CD8+ T cell epitope expressed in a cell infected with a different virus, if certain residues are retained in the correct position. A vaccine composition comprising one or more CD8+ T cell epitopes set out in SEQ ID NOs: 1 to 23 or a variant thereof, or a corresponding polynucleotide, may therefore be capable of providing cross-protection against a wide variety of existing flaviviruses over and above those recited in Table 1 and 2. Inclusion of one or more conserved peptides in the vaccine composition may also confer protective capability against emerging flavivirus strains associated with rapid evolution of the flavivirus genome. In this way, a single flavivirus vaccine composition can be used to confer protection against a variety of different flaviviruses. This provides a cost-effective means of controlling the spread of flavivirus infection.

Thirdly, different CD8+ T cell epitopes identified by the present inventors are capable of binding to different HLA supertypes. Inclusion of multiple peptides each comprising a CD8+ T cell epitope capable of binding to a different HLA supertypes (or corresponding polynucleotides) results in a vaccine composition that is effective in individuals having different HLA types. In this way, a single flavivirus vaccine composition can be used to confer protection in a large proportion of the human population. This again provides a cost-effective means of controlling the spread of flavivirus infection.

Fourthly, the flavivirus peptide comprised in the vaccine composition of the invention may be attached to a nanoparticle, for example a gold nanoparticle. As described in more detail below, attachment to a nanoparticle reduces or eliminates the need to include an adjuvant in the vaccine composition. Attachment to a nanoparticle also reduces or eliminates the need to include a virus in the vaccine composition Thus, the vaccine composition of the invention is less likely to cause adverse clinical effects upon administration to an individual.

Peptides

The vaccine composition of the invention comprises a flavivirus peptide comprising one or more of the CD8+ T cell epitopes set out in SEQ ID NOs: 1 to 23 or a variant thereof. Variants are defined in detail below. The vaccine composition may comprise from about one to about 50 such peptides, such as about 2 to 40, 3 to 30, 4 to 25, 5 to 20, 6 to 15, 7, 8, 9 or 10 such peptides. SEQ ID NOs: 1 to 23 are set out in Table 1.

TABLE 1

| SEQ ID NO: | Sequence | Protein ID | HLA affinity | Viral origin |
|---|---|---|---|---|
| 1 | IAVAVSSAIL | NS4B | A2 | Dengue/ZIKV |
| 2 | PMAAVGLLIVS | NS2B | A2/A24 | Dengue/ZIKV |
| 3 | WVTDHSGKTV | HELICc | A2 | Dengue/ZIKV/ West Nile |
| 4 | WVTDHSGKTV | FtsJ-like methyltransferase | A2 | Dengue/ZIKV/ HIV |
| 5 | IMLLGLLGTV | NS4A | A2 | ZIKV |
| 6 | ALGLTAVRLVD PI | E protein, transmembrane | A2/A24 | ZIKV |
| 7 | DESRAKVEVTP NSPR | Envelope glycoprotein | B44 | ZIKV |
| 8 | DPAVIGTAVK | NS1 | B7 | ZIKV |
| 9 | WPPSEVLTAVG | NS2 | B7 | ZIKV |
| 10 | DIGAVALDYPA | Peptidase S7, Flavivirus NS3 serine protease | A24 | ZIKV |
| 11 | EWEKRIAEAI | Non-structural polyprotein [Chikungunya virus] | A24 | Dengue/CHIK |
| 12 | FILLSMVGIAA | Envelope protein 2, partial [Chikungunya virus] | A2/24 | Dengue/CHIK |
| 13 | FLMCKTTDMV | Non-structural polyprotein [Chikungunya virus] | A2/24 | Dengue/CHIK |
| 14 | LQAVMAVPDT | Non-structural polyprotein [Chikungunya virus] | A2 | Dengue/CHIK |
| 15 | KLAEAIFKL | NS5 | A2/24 | DV2 |

TABLE 1-continued

| SEQ ID NO: | Sequence | Protein ID | HLA affinity | Viral origin |
|---|---|---|---|---|
| 16 | AMLSIPNAII | NS2A | A2/24 | DV2 |
| 17 | LLCVPNIMI | NS2A | A2/A24 | DV2 |
| 18 | TITEEIAVQ | NS4B | A2 | DV2 |
| 19 | LVMKDGRKL | NS5 | A2/3/24 | DV2 |
| 20 | LLGQGPMKLV | Protein C | A2/3/24 | DV2 |
| 21 | LMRNKGIGK | NS4A | A3 | DV2 |
| 22 | SPARLASAI | NS1 | B7 | DV2 |
| 23 | APTRVVAAEM EEAL | TBC | B7 | TBC |

The flavivirus peptide comprising one or more of the CD8+ T cell epitopes set out in SEQ ID NOs: 1 to 23 may comprise only one of the CD8+ T cell epitopes set out in SEQ ID NOs: 1 to 23. Alternatively, the flavivirus peptide comprising one or more of the CD8+ T cell epitopes set out in SEQ ID NOs: 1 to 23 may comprise two or more, such as three or more, four or more, five or more, six or more, seven or more, eight or more, nine or more, ten or more, 11 or more, 12 or more, 13 or more, 14 or more, 15 or more, 16 or more, 17 or more, 18 or more, 19 or more, 20 or more, 21 or more, or 22 or more of the CD8+ T cell epitopes set out in SEQ ID NOs: 1 to 23, in any combination. The flavivirus peptide comprising one or more of the CD8+ T cell epitopes set out in SEQ ID NOs: 1 to 23 may comprise all of the CD8+ T cell epitopes set out in SEQ ID NOs: 1 to 23.

The flavivirus peptide comprising one or more of the CD8+ T cell epitopes set out in SEQ ID NOs: 1 to 23 may comprise one or more of the CD8+ T cell epitopes set out in SEQ ID NOs: 1 to 14. The flavivirus peptide comprising one or more of the CD8+ T cell epitopes set out in SEQ ID NOs: 1 to 23 may comprise one or more of the CD8+ T cell epitopes set out in SEQ ID NOs: 15 to 23. For example, the flavivirus peptide comprising one or more of the CD8+ T cell epitopes set out in SEQ ID NOs: 1 to 23 may comprise (a) SEQ ID NO: 15 or a variant thereof, (b) SEQ ID NO: 16 or a variant thereof, (c) SEQ ID NO: 17 or a variant thereof, (d) SEQ ID NO: 18 or a variant thereof, (e) SEQ ID NO: 19 or a variant thereof, (f) SEQ ID NO: 20 or a variant thereof, (g) SEQ ID NO: 21 or a variant thereof, (h) SEQ ID NO: 22 or a variant thereof, or (i) SEQ ID NO: 23 or a variant thereof. The flavivirus peptide comprising one or more of the CD8+ T cell epitopes set out in SEQ ID NOs: 1 to 23 may, for example, comprise (a) and (b); (a) and (c); (a) and (d); (a) and (e); (a) and (f); (a) and (g); (a) and (h); (a) and (i); (b) and (c); (b) and (d); (b), and (e); (b) and (f); (b) and (g); (b) and (h); (b) and (i); (c) and (d); (c) and (e); (c) and (f); (c) and (g); (c) and (h); (c) and (i); (d) and (e); (d) and (f); (d) and (g); (d) and (h); (d) and (i); (e) and (f); (e) and (g); (e) and (h); (e) and (i); (f) and (g); (f) and (h); (f) and (i); (g) and (h); (g) and (i); (h) and (i); (a), (b) and (c); (a), (b) and (d); (a), (b) and (e); (a), (b) and (f); (a), (b) and (g); (a), (b) and (h); (a), (b) and (i); (a), (c) and (d); (a), (c) and (e); (a), (c) and (f); (a), (c) and (g); (a), (c) and (h); (a), (c) and (i); (a), (d) and (e); (a), (d) and (f); (a), (d) and (g); (a), (d) and (h); (a), (d) and (i); (a), (e), and (f); (a), (e) and (g); (a), (e) and (h); (a), (e) and (i); (a), (f) and (g); (a), (f) and (h); (a), (f) and (i); (a), (g) and (h); (a), (g) and (i); (a), (h) and (i); (b), (c) and (d); (b), (c) and (e); (b), (c) and (f); (b), (c) and (g); (b), (c) and (h); (b), (c) and (i); (b), (d) and (e); (b), (d) and (f); (b), (d) and (g); (b), (d) and (h); (b), (d) and (i); (b), (e) and (f); (b), (e) and (g); (b), (e) and (h); (b), (e) and (i); (b), (f) and (g); (b), (f) and (h); (b), (f) and (i); (b), (g) and (h); (b), (g) and (i); (b), (h) and (i); (c), (d) and (e); (c), (d) and (f); (c), (d) and (g); (c), (d) and (h); (c), (d) and (i); (c), (e) and (f); (c), (e) and (g); (c), (e) and (h); (c), (e) and (i); (c), (f) and (g); (c), (f) and (h); (c), (f) and (i); (c), (g) and (h); (c), (g) and (i); (c), (h) and (i); (d), (e) and (f); (d), (e) and (g); (d), (e) and (h); (d), (e) and (i); (d), (f) and (g); (d), (f) and (h); (d), (f) and (i); (d), (g) and (h); (d), (g) and (i); (d), (h) and (i); (e), (f) and (g); (e), (f) and (h); (e), (f) and (i); (e), (g) and (h); (e), (g) and (i); (e), (h) and (i); (f), (g), (h); (f), (g) and (i); (f), (h) and (i); (g), (h) and (i); (a), (b), (c), (d) and (e); (a), (b), (c), (d) and (f); (a), (b), (c), (d) and (g); (a), (b), (c), (d) and (h); (a), (b), (c), (d) and (i); (a), (b), (c), (e) and (f); (a), (b), (c), (e) and (g); (a), (b), (c), (e) and (h); (a), (b), (c), (e) and (i); (a), (b), (c), (f) and (g); (a), (b), (c), (f) and (h); (a), (b), (c), (f) and (i); (a), (b), (c), (g) and (h); (a), (b), (c), (g) and (i); (a), (b), (c), (h) and (i); (a), (b), (d), (e) and (f); (a), (b), (d), (e) and (g); (a), (b), (d), (e) and (h); (a), (b), (d), (e) and (i); (a), (b), (d), (f) and (g); (a), (b), (d), (f) and (h); (a), (b), (d), (f) and (i); (a), (b), (d), (g) and (h); (a), (b), (d), (g) and (i); (a), (b), (d), (h) and (i); (a), (b), (e), (f) and (g); (a), (b), (e), (f) and (h); (a), (b), (e), (f) and (i); (a), (b), (e), (g) and (h); (a), (b), (e), (g) and (i); (a), (b), (e), (h) and (i); (a), (b), (f), (g) and (h); (a), (b), (f), (g) and (i); (a), (b), (f), (h) and (i); (a), (b), (g), (h) and (i); (a), (c), (d), (e) and (f); (a), (c), (d), (e) and (g); (a), (c), (d), (e) and (h); (a), (c), (d), (e) and (i); (a), (c), (d), (f) and (g); (a), (c), (d), (f) and (h); (a), (c), (d), (f) and (i); (a), (c), (d), (g) and (h); (a), (c), (d), (g) and (i); (a), (c), (d), (h) and (i); (a), (c), (e), (f) and (g); (a), (c), (e), (f) and (h); (a), (c), (e), (f) and (i); (a), (c), (e), (g) and (h); (a), (c), (e), (g), (i); (a), (c), (e) and (h), (i); (a), (c), (f), (g) and (h); (a), (c), (f), (g) and (i); (a), (c), (f), (h) and (i); (a), (c), (g), (h) and (i); (a), (d), (e), (f) and (g); (a), (d), (e), (f) and (h); (a), (d), (e), (f) and (i); (a), (d), (e), (g) and (h); (a), (d), (e) and (g), (i); (a), (d), (e), (h) and (i); (a), (d), (f), (g) and (h); (a), (d), (f), (g) and (i); (a), (d), (f), (h) and (i); (a), (d), (g), (h) and (i); (a), (e), (f), (g) and (h); (a), (e), (f), (g) and (i); (a), (e), (f), (h) and (i); (a), (e), (g), (h) and (i); (a), (f), (g), (h) and (i); (b), (c), (d), (e) and (f); (b), (c), (d), (e) and (g); (b), (c), (d), (e)

and (h); (b), (c), (d), (e) and (i); (b), (c), (d), (f), and (g); (b), (c), (d), (f) and (h); (b), (c), (d), (f) and (i); (b), (c), (d), (g) and (h); (b), (c), (d), (g) and (i); (b), (c), (d), (h) and (i); (b), (c), (e), (f) and (g); (b), (c), (e), (f) and (h); (b), (c), (e), (f) and (i); (b), (c), (e), (g) and (h); (b), (c), (e), (g) and (i); (b), (c), (e), (h) and (i); (b), (c), (f), (g) and (h); (b), (c), (f), (g) and (i); (b), (c), (f), (h) and (i); (b), (c), (g), (h) and (i); (b), (d), (e), (f) and (g); (b), (d), (e), (f) and (h); (b), (d), (e), (f) and (i); (b), (d), (e), (g) and (h); (b), (d), (e), (g) and (i); (b), (d), (e) and (h), (i); (b), (d), (f), (g) and (h); (b), (d), (f), (g) and (i); (b), (d), (f), (h) and (i); (b), (d), (g), (h) and (i); (b), (e), (f), (g), and (h); (b), (e), (f), (g) and (i); (b), (e), (f), (h) and (i); (b), (e), (g), (h) and (i); (b), (f), (g), (h) and (i); (c), (d), (e) and (f), (g); (c), (d), (e), (f) and (h); (c), (d), (e), (f) and (i); (c), (d), (e), (g) and (h); (c), (d), (e), (g) and (i); (c), (d), (e), (h) and (i); (c), (d), (f), (g) and (h); (c), (d), (f), (g) and (i); (c), (d), (f), (h) and (i); (c), (d), (g), (h) and (i); (c), (e), (f), (g) and (h); (c), (e), (f), (g) and (i); (c), (e), (f), (h) and (i); (c), (e), (g), (h) and (i); (c), (f), (g), (h) and (i); (d), (e), (f), (g) and (h); (d), (e), (f), (g) and (i); (d), (e), (f), (h) and (i); (d), (e), (g), (h) and (i); (d), (f), (g), (h) and (i); (e), (f), (g), (h) and (i); (a), (b), (c), (d), (e) and (f); (a), (b), (c), (d), (e) and (g); (a), (b), (c), (d), (e) and (h); (a), (b), (c), (d), (e) and (i); (a), (b), (c), (d), (f) and (g); (a), (b), (c), (d), (f) and (h); (a), (b), (c), (d), (f) and (i); (a), (b), (c), (d), (g) and (h); (a), (b), (c), (d), (g) and (i); (a), (b), (c), (d), (h) and (i); (a), (b), (c), (e), (f) and (g); (a), (b), (c), (e), (f) and (h); (a), (b), (c), (e), (f) and (i); (a), (b), (c), (e), (g) and (h); (a), (b), (c), (e), (g) and (i); (a), (b), (c), (e), (h) and (i); (a), (b), (c), (f), (g) and (h); (a), (b), (c), (f), (g) and (i); (a), (b), (c), (f), (h) and (i); (a), (b), (c), (g), (h) and (i); (a), (b), (d), (e), (f) and (g); (a), (b), (d), (e), (f) and (h); (a), (b), (d), (e), (f) and (i); (a), (b), (d), (e), (g) and (h); (a), (b), (d), (e), (g) and (i); (a), (b), (d), (e), (h) and (i); (a), (b), (d), (f), (g) and (h); (a), (b), (d), (f), (g) and (i); (a), (b), (d), (f), (h) and (i); (a), (b), (d), (g), (h) and (i); (a), (b), (e), (f), (g) and (h); (a), (b), (e), (f), (g) and (i); (a), (b), (e), (f), (h) and (i); (a), (b), (e), (g), (h) and (i); (a), (b), (f), (g), (h) and (i); (a), (c), (d), (e), (f) and (g); (a), (c), (d), (e), (f) and (h); (a), (c), (d), (e), (f) and (i); (a), (c), (d), (e), (g) and (h); (a), (c), (d), (e), (g) and (i); (a), (c), (d), (e), (h) and (i); (a), (c), (d), (f), (g) and (h); (a), (c), (d), (f), (g) and (i); (a), (c), (d), (f), (h) and (i); (a), (c), (d), (g), (h), (i); (a), (c), (e), (f), (g), (h); (a), (c), (e), (f), (g), (i); (a), (c), (e), (f), (h), (i); (a), (c), (e), (g), (h) and (i); (a), (c), (f), (g), (h), (i); (a), (d), (e), (f), (g) and (h); (a), (d), (e), (f), (g) and (i); (a), (d), (e), (f), (h) and (i); (a), (d), (e), (g), (h) and (i); (a), (d), (f), (g), (h) and (i); (a), (e), (f), (g), (h) and (i); (b), (c), (d), (e), (f) and (g); (b), (c), (d), (e), (f) and (h); (b), (c), (d), (e), (f) and (i); (b), (c), (d), (e), (g) and (h); (b), (c), (d), (e), (g) and (i); (b), (c), (d), (e), (h) and (i); (b), (c), (d), (f), (g) and (h); (b), (c), (d), (f), (g) and (i); (b), (c), (d), (f), (h) and (i); (b), (c), (d), (g), (h) and (i); (b), (c), (e), (f), (g) and (h); (b), (c), (e), (f), (g) and (i); (b), (c), (e), (f), (h) and (i); (b), (c), (e), (g), (h) and (i); (b), (c), (f), (g), (h) and (i); (b), (d), (e), (f), (g) and (h); (b), (d), (e), (f), (g) and (i); (b), (d), (e), (f), (h) and (i); (b), (d), (e), (g), (h) and (i); (b), (d), (f), (g), (h) and (i); (b), (e), (f), (g), (h), and (i); (c), (d), (e), (f), (g) and (h); (c), (d), (e), (f), (g) and (i); (c), (d), (e), (f), (h) and (i); (c), (d), (e), (g), (h) and (i); (c), (d), (f), (g), (h) and (i); (c), (e), (f), (g), (h) and (i); (d), (e), (f), (g), (h) and (i); (a), (b), (c), (d), (e), (f) and (g); (a), (b), (c), (d), (e), (f) and (h); (a), (b), (c), (d), (e), (f) and (i); (a), (b), (c), (d), (e), (g) and (h); (a), (b), (c), (d), (e), (g) and (i); (a), (b), (c), (d), (e), (h) and (i); (a), (b), (c), (d), (f), (g) and (h); (a), (b), (c), (d), (f), (g) and (i); (a), (b), (c), (d), (f), (h) and (i); (a), (b), (c), (d), (g), (h) and (i); (a), (b), (c), (e), (f), (g) and (h); (a), (b), (c), (e), (f), (g) and (i); (a), (b), (c), (e), (f), (h)

and (i); (a), (b), (c), (e), (g), (h) and (i); (a), (b), (c), (f), (g), (h) and (i); (a), (b), (d), (e), (f), (g) and (h); (a), (b), (d), (e), (f), (g) and (i); (a), (b), (d), (e), (f), (h) and (i); (a), (b), (d), (e), (g), (h) and (i); (a), (b), (d), (f), (g), (h) and (i); (a), (b), (e), (f), (g), (h) and (i); (a), (c), (d), (e), (f), (g) and (h); (a), (c), (d), (e), (f), (g) and (i); (a), (c), (d), (e), (f), (h) and (i); (a), (c), (d), (e), (g), (h) and (i); (a), (c), (d), (f), (g), (h) and (i); (a), (c), (e), (f), (g), (h) and (i); (a), (d), (e), (f), (g), (h) and (i); (b), (c), (d), (e), (f), (g) and (h); (b), (c), (d), (e), (f), (g) and (i); (b), (c), (d), (e), (f), (h) and (i); (b), (c), (d), (e), (g), (h) and (i); (b), (c), (d), (f), (g), (h) and (i); (b), (c), (e), (f), (g), (h) and (i); (b), (d), (e), (f), (g), (h) and (i); (c), (d), (e), (f), (g), (h) and (i); (a), (b), (c), (d), (e), (f), (g) and (h); (a), (b), (c), (d), (e), (f), (g) and (i); (a), (b), (c), (d), (e), (f), (h) and (i); (a), (b), (c), (d), (e), (g), (h) and (i); (a), (b), (c), (d), (f), (g), (h) and (i); (a), (b), (c), (e), (f), (g), (h) and (i); (a), (b), (d), (e), (f), (g), (h) and (i); (a), (c), (d), (e), (f), (g), (h) and (i); (b), (c), (d), (e), (f), (g), (h) and (i); or (a), (b), (c), (d), (e), (f), (g), (h) and (i).

As well as one or more of the CD8+ T cell epitopes set out in SEQ ID NOs: 1 to 23, the flavivirus peptide may comprise one or more other CD8+ T cell epitopes, one or more CD4+ T cell epitopes and/or one or more B cell epitopes. For example, the flavivirus peptide may comprise two or more, such as three or more, four or more, five or more, ten or more, fifteen or more, or twenty or more CD8+ T cell epitopes other than those set out in SEQ ID NOs: 1 to 23. The flavivirus peptide may comprise two or more, such as three or more, four or more, five or more, ten or more, fifteen or more, or twenty or more CD4+ T cell epitopes. The flavivirus peptide may comprise two or more, such as three or more, four or more, five or more, ten or more, fifteen or more, or twenty or more B cell epitopes.

The vaccine composition may comprise two or more flavivirus peptides each comprising a CD8+ T cell epitope comprising a different sequence selected from SEQ ID NOs: 1 to 23. The vaccine composition may comprise two or more flavivirus peptides each comprising a CD8+ T cell epitope comprising a different sequence selected from SEQ ID NOs: 1 to 14 or a variant therefore. The vaccine composition may comprise two or more flavivirus peptides each comprising a CD8+ T cell epitope comprising a different sequence selected from SEQ ID NOs: 15 to 23 or a variant thereof. Each of the flavivirus peptides may have any of the properties set out in the preceding paragraphs. For instance, each flavivirus peptide may comprise multiple CD8+ T cell epitopes set out in SEQ ID NOs: 1 to 23 or a variant thereof and, optionally, one or more other CD8+ T cell epitopes, one or more CD4+ T cell epitopes and/or one or more B cell epitopes. In one aspect, the vaccine composition may comprise three or more, four or more, five or more, six or more, seven or more, eight or more, nine or more, ten or more, 11 or more, 12 or more, 13 or more, 14 or more, 15 or more, 16 or more, 17 or more, 18 or more, 19 or more, 20 or more, 21 or more, or 22 or more flavivirus peptides each comprising a CD8+ T cell epitope comprising a different sequence selected from SEQ ID NOs: 1 to 23 or a variant thereof. The vaccine composition may, for example, comprise 23 flavivirus peptides each comprising a CD8+ T cell epitope comprising a different sequence selected from SEQ ID NOs: 1 to 23 or a variant thereof. The vaccine composition may, for example, comprise 14 flavivirus peptides each comprising a CD8+ T cell epitope comprising a different sequence selected from SEQ ID NOs: 1 to 14 or a variant thereof. The vaccine composition may, for example, comprise 9 flavivirus peptides each comprising a CD8+ T cell epitope comprising a different sequence selected from SEQ ID NOs: 15 to 23 or a variant thereof.

The vaccine composition may, for example, comprise two or more flavivirus peptides selected from SEQ ID NOs: 15 to 23 in one of the following combinations in which (a) is SEQ ID NO: 15 or a variant thereof, (b) is SEQ ID NO: 16 or a variant thereof, (c) is SEQ ID NO: 17 or a variant thereof, (d) is SEQ ID NO: 18 or a variant thereof, (e) is SEQ ID NO: 19 or a variant thereof, (f) is SEQ ID NO: 20 or a variant thereof, (g) is SEQ ID NO: 21 or a variant thereof, (h) is SEQ ID NO: 22 or a variant thereof, and (i) is SEQ ID NO: 23 or a variant thereof: (a) and (b); (a) and (c); (a) and (d); (a) and (e); (a) and (f); (a) and (g); (a) and (h); (a) and (i); (b) and (c); (b) and (d); (b), and (e); (b) and (f); (b) and (g); (b) and (h); (b) and (i); (c) and (d); (c) and (e); (c) and (f); (c) and (g); (c) and (h); (c) and (i); (d) and (e); (d) and (f); (d) and (g); (d) and (h); (d) and (i); (e) and (f); (e) and (g); (e) and (h); (e) and (i); (f) and (g); (f) and (h); (f) and (i); (g) and (h); (g) and (i); (h) and (i); (a), (b) and (c); (a), (b) and (d); (a), (b) and (e); (a), (b) and (f); (a), (b) and (g); (a), (b) and (h); (a), (b) and (i); (a), (c) and (d); (a), (c) and (e); (a), (c) and (f); (a), (c) and (g); (a), (c) and (h); (a), (c) and (i); (a), (d) and (e); (a), (d) and (f); (a), (d) and (g); (a), (d) and (h); (a), (d) and (i); (a), (e), and (f); (a), (e) and (g); (a), (e) and (h); (a), (e) and (i); (a), (f) and (g); (a), (f) and (h); (a), (f) and (i); (a), (g) and (h); (a), (g) and (i); (a), (h) and (i); (b), (c) and (d); (b), (c) and (e); (b), (c) and (f); (b), (c) and (g); (b), (c) and (h); (b), (c) and (i); (b), (d) and (e); (b), (d) and (f); (b), (d) and (g); (b), (d) and (h); (b), (d) and (i); (b), (e) and (f); (b), (e) and (g); (b), (e) and (h); (b), (e) and (i); (b), (f) and (g); (b), (f) and (h); (b), (f) and (i); (b), (g) and (h); (b), (g) and (i); (b), (h) and (i); (c), (d) and (e); (c), (d) and (f); (c), (d) and (g); (c), (d) and (h); (c), (d) and (i); (c), (e) and (f); (c), (e) and (g); (c), (e) and (h); (c), (e) and (i); (c), (f) and (g); (c), (f) and (h); (c), (f) and (i); (c), (g) and (h); (c), (g) and (i); (c), (h) and (i); (d), (e) and (f); (d), (e) and (g); (d), (e) and (h); (d), (e) and (i); (d), (f) and (g); (d), (f) and (h); (d), (f) and (i); (d), (g) and (h); (d), (g) and (i); (d), (h) and (i); (e), (f) and (g); (e), (f) and (h); (e), (f) and (i); (e), (g) and (h); (e), (g) and (i); (e), (h) and (i); (f), (g), (h); (f), (g) and (i); (f), (h) and (i); (g), (h) and (i); (a), (b), (c), (d) and (e); (a), (b), (c), (d) and (f); (a), (b), (c), (d) and (g); (a), (b), (c), (d) and (h); (a), (b), (c), (d) and (i); (a), (b), (c), (e) and (f); (a), (b), (c), (e) and (g); (a), (b), (c), (e) and (h); (a), (b), (c), (e) and (i); (a), (b), (c), (f) and (g); (a), (b), (c), (f) and (h); (a), (b), (c), (f) and (i); (a), (b), (c), (g) and (h); (a), (b), (c), (g) and (i); (a), (b), (c), (h) and (i); (a), (b), (d), (e) and (f); (a), (b), (d), (e) and (g); (a), (b), (d), (e) and (h); (a), (b), (d), (e) and (i); (a), (b), (d), (f) and (g); (a), (b), (d), (f) and (h); (a), (b), (d), (f) and (i); (a), (b), (d), (g) and (h); (a), (b), (d), (g) and (i); (a), (b), (d), (h) and (i); (a), (b), (e), (f) and (g); (a), (b), (e), (f) and (h); (a), (b), (e), (f) and (i); (a), (b), (e), (g) and (h); (a), (b), (e), (g) and (i); (a), (b), (e), (h) and (i); (a), (b), (f), (g) and (h); (a), (b), (f), (g) and (i); (a), (b), (f), (h) and (i); (a), (b), (g), (h) and (i); (a), (c), (d), (e) and (f); (a), (c), (d), (e) and (g); (a), (c), (d), (e) and (h); (a), (c), (d), (e) and (i); (a), (c), (d), (f) and (g); (a), (c), (d), (f) and (h); (a), (c), (d), (f) and (i); (a), (c), (d), (g) and (h); (a), (c), (d), (g) and (i); (a), (c), (d), (h) and (i); (a), (c), (e), (f) and (g); (a), (c), (e), (f) and (h); (a), (c), (e), (f) and (i); (a), (c), (e), (g) and (h); (a), (c), (e), (g), (i); (a), (c), (e) and (h), (i); (a), (c), (f), (g) and (h); (a), (c), (f), (g) and (i); (a), (c), (f), (h) and (i); (a), (c), (g), (h) and (i); (a), (d), (e), (f) and (g); (a), (d), (e), (f) and (h); (a), (d), (e), (f) and (i); (a), (d), (e), (g) and (h); (a), (d), (e) and (g), (i); (a), (d), (e), (h) and (i); (a), (d), (f), (g) and (h); (a), (d), (f), (g) and (i); (a), (d), (f), (h) and (i); (a), (d), (g), (h) and (i); (a), (e), (f), (g) and (h); (a), (e), (f), (g) and (i); (a), (e), (f), (h) and (i); (a), (e), (g), (h) and (i); (a), (f), (g), (h) and (i); (b), (c), (d), (e) and (f); (b), (c), (d), (e) and (g); (b), (c), (d), (e) and (h); (b), (c), (d), (e) and (i); (b), (c), (d), (f), and (g); (b), (c), (d), (f) and (h); (b), (c), (d), (f) and (i); (b), (c), (d), (g) and (h); (b), (c), (d), (g) and (i); (b), (c), (d), (h) and (i); (b), (c), (e), (f) and (g); (b), (c), (e), (f) and (h); (b), (c), (e), (f) and (i); (b), (c), (e), (g) and (h); (b), (c), (e), (g) and (i); (b), (c), (e), (h) and (i); (b), (c), (f), (g) and (h); (b), (c), (f), (g) and (i); (b), (c), (f), (h) and (i); (b), (c), (g), (h) and (i); (b), (d), (e), (f) and (g); (b), (d), (e), (f) and (h); (b), (d), (e), (f) and (i); (b), (d), (e), (g) and (h); (b), (d), (e), (g) and (i); (b), (d), (e) and (h), (i); (b), (d), (f), (g) and (h); (b), (d), (f), (g) and (i); (b), (d), (f), (h) and (i); (b), (d), (g), (h) and (i); (b), (e), (f), (g), and (h); (b), (e), (f), (g) and (i); (b), (e), (f), (h) and (i); (b), (e), (g), (h) and (i); (b), (f), (g), (h) and (i); (c), (d), (e) and (f), (g); (c), (d), (e), (f) and (h); (c), (d), (e), (f) and (i); (c), (d), (e), (g) and (h); (c), (d), (e), (g) and (i); (c), (d), (e), (h) and (i); (c), (d), (f), (g) and (h); (c), (d), (f), (g) and (i); (c), (d), (f), (h) and (i); (c), (d), (g), (h) and (i); (c), (e), (f), (g) and (h); (c), (e), (f), (g) and (i); (c), (e), (f), (h) and (i); (c), (e), (g), (h) and (i); (c), (f), (g), (h) and (i); (d), (e), (f), (g) and (h); (d), (e), (f), (g) and (i); (d), (e), (f), (h) and (i); (d), (e), (g), (h) and (i); (d), (f), (g), (h) and (i); (e), (f), (g), (h) and (i); (a), (b), (c), (d), (e) and (f); (a), (b), (c), (d), (e) and (g); (a), (b), (c), (d), (e) and (h); (a), (b), (c), (d), (e) and (i); (a), (b), (c), (d), (f) and (g); (a), (b), (c), (d), (f) and (h); (a), (b), (c), (d), (f) and (i); (a), (b), (c), (d), (g) and (h); (a), (b), (c), (d), (g) and (i); (a), (b), (c), (d), (h) and (i); (a), (b), (c), (e), (f) and (g); (a), (b), (c), (e), (f) and (h); (a), (b), (c), (e), (f) and (i); (a), (b), (c), (e), (g) and (h); (a), (b), (c), (e), (g) and (i); (a), (b), (c), (e), (h) and (i); (a), (b), (c), (f), (g) and (h); (a), (b), (c), (f), (g) and (i); (a), (b), (c), (f), (h) and (i); (a), (b), (c), (g), (h) and (i); (a), (b), (d), (e), (f) and (g); (a), (b), (d), (e), (f) and (h); (a), (b), (d), (e), (f) and (i); (a), (b), (d), (e), (g) and (h); (a), (b), (d), (e), (g) and (i); (a), (b), (d), (e), (h) and (i); (a), (b), (d), (f), (g) and (h); (a), (b), (d), (f), (g) and (i); (a), (b), (d), (f), (h) and (i); (a), (b), (d), (g), (h) and (i); (a), (b), (e), (f), (g) and (h); (a), (b), (e), (f), (g) and (i); (a), (b), (e), (f), (h) and (i); (a), (b), (e), (g), (h) and (i); (a), (b), (f), (g), (h) and (i); (a), (c), (d), (e), (f) and (g); (a), (c), (d), (e), (f) and (h); (a), (c), (d), (e), (f) and (i); (a), (c), (d), (e), (g) and (h); (a), (c), (d), (e), (g) and (i); (a), (c), (d), (e), (h) and (i); (a), (c), (d), (f), (g) and (h); (a), (c), (d), (f), (g) and (i); (a), (c), (d), (f), (h) and (i); (a), (c), (d), (g), (h), (i); (a), (c), (e), (f), (g), (h); (a), (c), (e), (f), (g), (i); (a), (c), (e), (f), (h), (i); (a), (c), (e), (g), (h) and (i); (a), (c), (f), (g), (h), (i); (a), (d), (e), (f), (g) and (h); (a), (d), (e), (f), (g) and (i); (a), (d), (e), (f), (h) and (i); (a), (d), (e), (g), (h) and (i); (a), (d), (f), (g), (h) and (i); (a), (e), (f), (g), (h) and (i); (b), (c), (d), (e), (f) and (g); (b), (c), (d), (e), (f) and (h); (b), (c), (d), (e), (f) and (i); (b), (c), (d), (e), (g) and (h); (b), (c), (d), (e), (g) and (i); (b), (c), (d), (e), (h) and (i); (b), (c), (d), (f), (g) and (h); (b), (c), (d), (f), (g) and (i); (b), (c), (d), (f), (h) and (i); (b), (c), (d), (g), (h) and (i); (b), (c), (e), (f), (g) and (h); (b), (c), (e), (f), (g) and (i); (b), (c), (e), (f), (h) and (i); (b), (c), (e), (g), (h) and (i); (b), (c), (f), (g), (h) and (i); (b), (d), (e), (f), (g) and (h); (b), (d), (e), (f), (g) and (i); (b), (d), (e), (f), (h) and (i); (b), (d), (e), (g), (h) and (i); (b), (d), (f), (g), (h) and (i); (b), (e), (f), (g), (h), and (i); (c), (d), (e), (f), (g) and (h); (c), (d), (e), (f), (g) and (i); (c), (d), (e), (f), (h) and (i); (c), (d), (e), (g), (h) and (i); (c), (d), (f), (g), (h) and (i); (c), (e), (f), (g), (h) and (i); (d), (e), (f), (g), (h) and (i); (a), (b), (c), (d), (e), (f) and (g); (a), (b), (c), (d), (e), (f) and (h); (a), (b), (c), (d), (e), (f) and (i); (a), (b), (c), (d), (e), (g) and (h); (a), (b), (c), (d), (e), (g) and (i); (a), (b), (c), (d), (e), (h) and (i); (a), (b), (c), (d), (f), (g) and (h); (a), (b), (c), (d), (f), (g) and (i); (a), (b), (c), (d), (f), (h) and (i); (a), (b), (c), (d), (g), (h) and (i); (a), (b), (c), (e), (f), (g) and (h); (a), (b), (c), (e), (f), (g) and (i); (a), (b), (c), (e), (f), (h) and (i); (a), (b), (c), (e), (g), (h) and (i); (a), (b), (c), (f), (g), (h) and (i); (a), (b), (d), (e), (f), (g) and (h); (a), (b), (d), (e), (f), (g) and (i); (a), (b), (d), (e), (f), (h) and (i); (a), (b), (d), (e), (g), (h) and (i); (a), (b), (d), (f), (g), (h) and (i); (a), (b), (e), (f), (g), (h) and (i); (a), (c), (d), (e), (f), (g) and (h); (a), (c), (d), (e), (f), (g) and (i); (a), (c), (d), (e), (f), (h) and (i); (a), (c), (d), (e), (g), (h) and (i); (a), (c), (d), (f), (g), (h) and (i); (a), (c), (e), (f), (g), (h) and (i); (a), (d), (e), (f), (g), (h) and (i); (b), (c), (d), (e), (f), (g) and (h); (b), (c), (d), (e), (f), (g) and (i); (b), (c), (d), (e), (f), (h) and (i); (b), (c), (d), (e), (g), (h) and (i); (b), (c), (d), (f), (g), (h) and (i); (b), (c), (e), (f), (g), (h) and (i); (b), (d), (e), (f), (g), (h) and (i); (c), (d), (e), (f), (g), (h) and (i); (a), (b), (c), (d), (e), (f), (g) and (h); (a), (b), (c), (d), (e), (f), (g) and (i); (a), (b), (c), (d), (e), (f), (h) and (i); (a), (b), (c), (d), (e), (g), (h) and (i); (a), (b), (c), (d), (f), (g), (h) and (i); (a), (b), (c), (e), (f), (g), (h) and (i); (a), (b), (d), (e), (f), (g), (h) and (i); (a), (c), (d), (e), (f), (g), (h) and (i); (b), (c), (d), (e), (f), (g), (h) and (i); or (a), (b), (c), (d), (e), (f), (g), (h) and (i).

The vaccine composition may further comprise one or more (such as about 1 to 50, 2 to 40, 3 to 30, 4 to 25, 5 to 20, 6 to 15, 7, 8, 10 or 10) additional peptides each comprising one or more epitopes. The epitope may be a CD8+ T cell epitope, a CD4+ T cell epitope and/or a B cell epitope. The CD8+ T cell epitope is preferably a CD8+ T cell epitope other than the CD8+ T cell epitopes set out in SEQ ID NOs: 1 to 23 or a variant thereof. The CD8+ T cell epitope may, for example, be a flavivirus CD8+ epitope, i.e. a peptide that is expressed by one or more flaviviruses and that is that is capable of (i) presentation by a class I MHC molecule and (ii) recognition by a T cell receptor (TCR) present on a CD8+ T cell. Alternatively, the CD8+ T cell epitope may be an CD8+ T cell epitope that is not expressed by one or more flaviviruses. The CD4+ T cell epitope may, for example, be a flavivirus CD4+ epitope, i.e. a peptide that is expressed by one or more flaviviruses and that is that is capable of (i) presentation by a class II MHC molecule and (ii) recognition by a T cell receptor (TCR) present on a CD4+ T cell. Alternatively, the CD4+ T cell epitope may be an CD4+ T cell epitope that is not expressed by one or more flaviviruses. CD8+ and CD4+ T cell epitopes are described in more detail below.

A flavivirus peptide is a peptide that is expressed by one or more flaviviruses. Numerous species of flavivirus exist, including Zika virus, Dengue virus, West Nile virus and yellow fever virus, as well as St. Louis encephalitis virus, Japanese encephalitis virus, Murray Valley encephalitis virus, Tick-borne encephalitis virus, Kunjin encephalitis virus, Rocio encephalitis virus, Russian Spring Summer encephalitis virus, Negeishi virus, Kyasanur Forest virus, Omsk Hemorrhagic Fever virus, Powassan virus, Louping Ill virus, Rio Bravo virus, Tyuleniy virus, Ntaya virus and Modoc virus. There are four serotypes of Dengue virus (DENV-1, DENV-2, DENV-3 and DENV-4) and two strains of Zika virus (African Zika virus and Asian Zika virus).

Any flavivirus peptide comprised in the vaccine composition of the invention may comprise a peptide that is expressed by one or more of Zika virus, Dengue virus, West Nile virus, yellow fever virus, St. Louis encephalitis virus, Japanese encephalitis virus, Murray Valley encephalitis virus, Tick-borne encephalitis virus, Kunjin encephalitis virus, Rocio encephalitis virus, Russian Spring Summer encephalitis virus, Negeishi virus, Kyasanur Forest virus, Omsk Hemorrhagic Fever virus, Powassan virus, Louping Ill virus, Rio Bravo virus, Tyuleniy virus, Ntaya virus and Modoc virus. For example, a flavivirus peptide comprised in the vaccine composition of the invention may comprise a peptide that is expressed by Zika virus and Dengue virus, or Zika virus, Dengue virus and West Nile virus. For instance, the flavivirus peptide comprising one or more of the CD8+ T cell epitopes set out in SEQ ID NOs: 1 to 23 or a variant thereof may be expressed by (i) one or more of Zika virus, Dengue virus, West Nile virus, yellow fever virus, St. Louis encephalitis virus, Japanese encephalitis virus, Murray Valley encephalitis virus, Tick-borne encephalitis virus, Kunjin encephalitis virus, Rocio encephalitis virus, Russian Spring Summer encephalitis virus, Negeishi virus, Kyasanur Forest virus, Omsk Hemorrhagic Fever virus, Powassan virus, Louping Ill virus, Rio Bravo virus, Tyuleniy virus, Ntaya virus and Modoc virus; (ii) Zika virus and Dengue virus; or (iii) Zika virus, Dengue virus and West Nile virus. Likewise, when the composition comprises an additional peptide that is a flavivirus peptide, that additional filovirus peptide may be expressed by (i) one or more of Zika virus, Dengue virus, West Nile virus, yellow fever virus, St. Louis encephalitis virus, Japanese encephalitis virus, Murray Valley encephalitis virus, Tick-borne encephalitis virus, Kunjin encephalitis virus, Rocio encephalitis virus, Russian Spring Summer encephalitis virus, Negeishi virus, Kyasanur Forest, Omsk Hemorrhagic Fever virus, Powassan virus, Louping Ill virus, Rio Bravo virus, Tyuleniy virus, Ntaya virus and Modoc virus; (ii) Zika virus and Dengue virus; or (iii) Zika virus, Dengue virus and West Nile virus. Accordingly, the vaccine composition may comprise flavivirus peptides from one or more species of flavivirus, such as 1 to 20, 2 to 19, 3 to 18, 4 to 17, 5 to 16, 6 to 15, 7 to 14, 8 to 13, 9 to 12, 10 or 11 species of flavivirus.

When a flavivirus peptide comprised in the vaccine composition of the invention comprises a peptide that is expressed by Zika virus, the peptide may be expressed by African Zika virus, Asian Zika virus, or both African Zika virus and Asian Zika virus. When a flavivirus peptide comprised in the vaccine composition of the invention comprises a peptide that is expressed by Dengue virus, the peptide may be expressed by one or more of DENV-1, DENV-2, DENV-3 and DENV-4 in any combination such as, for example: 1; 2; 3; 4; 1 and 2; 1 and 3; 1 and 4; 2 and 3; 2 and 4; 3 and 4; 1, 2 and 3; 1, 2 and 4; 1, 3 and 4; 2, 3 and 4; or 1, 2, 3 and 4.

The flavivirus peptide may be a peptide that is expressed on the surface of one or more flaviviruses, or intracellularly within one or more flaviviruses. The peptide may be a structural peptide or a functional peptide, such as a peptide involved in the metabolism or replication of the flavivirus. Preferably, the peptide is an internal peptide. Preferably, the peptide is conserved between two or more different flaviviruses or flavivirus serotypes. A peptide is conserved between two or more different flaviviruses or flavivirus serotypes if each of the two or more different flaviviruses or flavivirus serotypes encodes a sequence that is 50% or more (such as 60%, 70%, 75%, 80%, 90%, 95%, 98% or 99%) homologous to the peptide.

The flavivirus peptide may contain any number of amino acids, i.e. be of any length. Typically, the flavivirus peptide is about 8 to about 30, 35 or 40 amino acids in length, such as about 9 to about 29, about 10 to about 28, about 11 to about 27, about 12 to about 26, about 13 to about 25, about 13 to about 24, about 14 to about 23, about 15 to about 22, about 16 to about 21, about 17 to about 20, or about 18 to about 29 amino acids in length.

The flavivirus peptide may be chemically derived from a polypeptide flavivirus antigen, for example by proteolytic cleavage. More typically, the flavivirus peptide may be synthesised using methods well known in the art.

The term "peptide" includes not only molecules in which amino acid residues are joined by peptide (—CO—NH—) linkages but also molecules in which the peptide bond is reversed. Such retro-inverso peptidomimetics may be made using methods known in the art, for example such as those described in Meziere et al (1997) J. Immunol. 159, 3230-3237. This approach involves making pseudopeptides containing changes involving the backbone, and not the orientation of side chains. Meziere et al (1997) show that, at least for MHC class II and T helper cell responses, these pseudopeptides are useful. Retro-inverse peptides, which contain NH—CO bonds instead of CO—NH peptide bonds, are much more resistant to proteolysis.

Similarly, the peptide bond may be dispensed with altogether provided that an appropriate linker moiety which retains the spacing between the carbon atoms of the amino acid residues is used; it is particularly preferred if the linker moiety has substantially the same charge distribution and substantially the same planarity as a peptide bond. It will also be appreciated that the peptide may conveniently be blocked at its N- or C-terminus so as to help reduce susceptibility to exoproteolytic digestion. For example, the N-terminal amino group of the peptides may be protected by reacting with a carboxylic acid and the C-terminal carboxyl group of the peptide may be protected by reacting with an amine. Other examples of modifications include glycosylation and phosphorylation. Another potential modification is that hydrogens on the side chain amines of R or K may be replaced with methylene groups (—NH2 may be modified to —NH(Me) or —$N(Me)_2$).

The term "peptide" also includes peptide variants that increase or decrease the half-life of the peptide in vivo. Examples of analogues capable of increasing the half-life of peptides used according to the invention include peptoid analogues of the peptides, D-amino acid derivatives of the peptides, and peptide-peptoid hybrids. A further embodiment of the variant polypeptides used according to the invention comprises D-amino acid forms of the polypeptide. The preparation of polypeptides using D-amino acids rather than L-amino acids greatly decreases any unwanted breakdown of such an agent by normal metabolic processes, decreasing the amounts of agent which needs to be administered, along with the frequency of its administration.

Variants

As set out above, the vaccine composition of the invention may comprise a flavivirus peptide comprising a variant of one or more of the CD8+ T cell epitopes set out in SEQ ID NOs: 1 to 23. A variant of a sequence selected from SEQ ID NOs: 1 to 23 is a CD8+ T cell epitope that differs from the relevant sequence by no more than one amino acid. For example, a variant of a sequence selected from SEQ ID NOs: 1 to 23 may comprise one amino acid substitution, deletion or insertion relative to the relevant sequence. The amino acid substitution may, for example, be a conservative amino acid substitution.

Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 2 below. Where amino acids have similar polarity, this can also be determined by reference to the hydropathy scale for amino acid side chains in Table 3.

TABLE 2

Chemical properties of amino acids

| | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged (+) | Trp | aromatic, hydrophobic, neutral |
| Leu | aliphatic, hydrophobic, neutral | Tyr | aromatic, polar, hydrophobic |

TABLE 3

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

CD8+ T Cell Epitopes

The vaccine composition of the invention comprises a flavivirus peptide comprising one or more of the CD8+ T cell epitopes set out in SEQ ID NOs: 1 to 23 (see Table 1) or a variant thereof. Variants are defined above. The flavivirus peptide comprising one or more of the CD8+ T cell epitopes set out in SEQ ID NOs: 1 to 23 or a variant thereof may further comprise one or more (such as two or more, three or more, four or more, five or more, ten or more, fifteen or more, or twenty or more) other CD8+ T cell epitopes. The vaccine composition may further comprise one or more (such as 1 to 50, 2 to 40, 3 to 30, 4 to 25, 5 to 20, 6 to 15, 7, 8, 9 or 10) additional peptides each comprising one or more CD8+ T cell epitopes. Preferably, the additional peptide is a flavivirus peptide.

A CD8+ T cell epitope is a peptide that is capable of (i) presentation by a class I MHC molecule and (ii) recognition by a T cell receptor (TCR) present on a CD8+ T cell. Preferably, recognition by the TCR results in activation of the CD8+ T cell. CD8+ T cell activation may lead to increased proliferation, cytokine production and/or cyotoxic effects.

Typically, the CD8+ T cell epitope is around 9 amino acids in length. The CD8+ T cell epitope may though be shorter or longer. For example, the CD8+ T cell epitope may be about 8, 9, 10, 11, 12, 13, 14 or 15 amino acids in length. The CD8+ T cell epitope may be about 8 to 15, 9 to 14 or 10 to 12 amino acids in length.

Flavivirus peptides comprising a CD8+ T cell epitope are known in the art. Methods for identifying CD8+ T cell epitopes are known in the art. Epitope mapping methods include X-ray co-crystallography, array-based oligo-peptide scanning (sometimes called overlapping peptide scan or pepscan analysis), site-directed mutagenesis, high throughput mutagenesis mapping, hydrogen-deuterium exchange, crosslinking coupled mass spectrometry, phage display and limited proteolysis. MHC motif prediction methodologies may also be used.

CD8+ T cell epitopes presented by flavivirus-infected cells can be identified in order to directly identify CD8+ T cell epitopes for inclusion in the vaccine composition. This is an efficient and logical method which can be used alone or to confirm the utility of potential CD8+ T cell epitopes identified by MHC motif prediction methodologies. This method was used by the inventors to identify the CD8+ T cell epitopes set out in SEQ ID NOs: 1 to 23 (see Examples).

To perform the method, cells are infected with a flavivirus and maintained in culture for a period of around 72 hours at a temperature of around 37° C. Following culture, the cells are then harvested and washed. Next, the cells are lysed, for instance by homogenisation and freezing/thawing in buffer containing 1% NP40. Lysates are cleared by centrifugation at 2000 rpm for 30 minutes to remove cell debris.

MHC/peptide complexes are then isolated from the lysates by immunoaffinity chromatography using protein A/G beads (UltraLink Immobilized Protein A/G, pierce, Rockford, IL) coated with W6/32 (a monoclonal antibody recognising pan MHC class I molecule). To coat the beads with the antibody, the beads are washed with low pH buffer followed by PBS rinses, incubated with 0.5 mg of the antibody at room temperature for 2 hours, and washed three times to remove unbound antibody. For immunoaffinity chromatography, the coated beads are incubate with lysate for 2 hours at room temperature with continuous rocking. The beads are then separated from the lysate by centrifuging at 1000 rpm for 5 minutes. Bound MHC complexes are eluted from the beads by the addition of 0.1% trifluoroacetic acid (TFA), pH 1.5.

The eluate is next heated at 85° C. for 15 minutes to dissociate the bound peptides from the MHC molecules. After cooling to room temperature, peptides are separated from the antibody by centrifugation using, for example, 3 kDa molecular mass cutoff membrane filters (Millipore). The filtrate is concentrated using vacuum centrifugation and reconstituted to a final volume of 1001. The purified peptide mixture is fractionated, for example using a C-18 reversed phase (RP) column (e.g. 4.6 mm diameter×150 mm length) using an offline HPLC. For this step, mobile phase A may be 2% acetonitrile (CAN) and 0.1% formic acid (FA) in water, while mobile phase B may be 0.1% FA and 90% CAN in water.

The peptide-containing fractions are then eluted from the column, dried under a vacuum, and analysed by mass spectrometry to identify the sequences of the fractions. The acquired spectral data can then be searched against all databased flavivirus proteins to identify peptide sequences associated with flavivirus. Synthetic peptides may then be made according to the identified sequences and subjected to mass spectrometry to confirm their identity to the peptides in the peptide-containing fractions.

In this method, any type of cells may be infected with flavivirus. The cells may be antigen presenting cells. The cells may be hepatoma cells such as HepG2 cells, EBV-transformed lymphoblastoid B cells such as JY cells, or lymphoblasts such as T2 cells.

Likewise, any flavivirus of interest may be used to infect the cells. For instance, the flavivirus may be Zika virus, Dengue virus, West Nile virus, yellow fever virus, St. Louis encephalitis virus, Japanese encephalitis virus, Murray Valley encephalitis virus, Tick-borne encephalitis virus, Kunjin encephalitis virus, Rocio encephalitis virus, Russian Spring Summer encephalitis virus, Negeishi virus, Kyasanur Forest, Omsk Hemorrhagic Fever virus, Powassan virus, Louping Ill virus, Rio Bravo virus, Tyuleniy virus, Ntaya virus and Modoc virus. The Zika virus may, for example, be African Zika Virus or Asian Zika Virus. The Dengue virus may, for example, be DENV-1, DENV-2, DENV-3 or DENV-4.

The direct identification of CD8+ T cell epitopes presented by flavivirus-infected cells is advantageous compared to MHC motif prediction methodologies. The immune epitope database (IEDB; http://www.iedb.org) is generated by motif prediction methods, and not functional methods, and contains numerous predicted HLA-specific flavivirus T cell epitopes, including some shared epitopes with high MHC binding scores and limited CTL characterization. As both dominant and subdominant epitopes may be presented by flavivirus-infected cells, it is difficult to sort out the dominance hierarchies of naturally presented epitopes using the database. Thus, it is not clear from the immune epitope database alone which of the listed epitopes may be expected to efficiently induce a CD8+ T cell response when included in a vaccine composition. The direct identification method set out above provides a mechanism for confirming the utility of the epitopes.

Vaccine compositions based on epitopes presented by flavivirus-infected cells, such as the vaccine composition of the invention, are superior to vaccines based on a viral protein subunit or a motif predicted epitope. Protein processing by the immune system is likely to alter native viral epitopes. Basing a vaccine composition on peptides demonstrated to be presented by infected cells removes this source of uncertainty, because the peptides have already undergone protein processing.

Furthermore, the direct identification method may be used to identify conserved CD8+ T cell epitopes presented by cells infected by different flaviviruses. In this way, CD8+ T cell epitopes suitable for inclusion in a cross-protective vaccine may be identified. As set out in Table 1 above and in the Examples, the present inventors have identified a number of CD8+ T cell epitopes conserved between two or more.

Cross-Protective Vaccine Compositions

Many of SEQ ID NOs: 1 to 23 identified by the present inventors are expressed by multiple flaviviruses. For instance, SEQ ID NOs: 1, 2 and 4 are expressed by Dengue virus and Zika virus; and SEQ ID No: 3 is expressed by Dengue virus, Zika virus and West Nile virus. Furthermore, SEQ ID NOs: 1 to 23 are highly conserved between flaviviruses. The vaccine composition of the invention may therefore elicit a protective immune response against more than one flavivirus. In other words, the vaccine composition of the invention may elicit an immune response that is cross-protective against a number of different flaviviruses.

Many of SEQ ID NOs: 1 to 23 identified by the present inventors are expressed by a flavivirus (e.g. Dengue virus) and also by Chikungunya virus. For instance, SEQ ID NOs: 11, 12, 13 and 14 are expressed by Dengue virus and Chikungunya virus. The vaccine composition of the invention may therefore elicit an immune response that is protective against one or more flavivirus (such as Dengue virus and/or Zika virus), and Chikungunya virus. The vaccine composition may be a triple vaccine composition effective against Dengue virus, Zika virus and Chikungunya virus, which may all be transmitted by the same species of mosquito.

An immune response generated by vaccination with a composition that comprises an epitope that is 100% homologous with a sequence from another virus may protect against subsequent infection with that virus. An immune response generated by vaccination with a composition that comprises an epitope that is about 50% or more (such as 60%, 70%, 75%, 80%, 90%, 95%, 98% or 99%) homologous with a sequence encoded by another virus may protect against subsequent infection with that virus. In some cases, the protective effect is associated with the conservation of certain residues between the epitope and the sequence encoded by the other virus. Immunisation with a vaccine composition of the invention may therefore induce a protective immune response against a wide variety of viruses not mentioned in Table 1 or Table 4, such as other flaviviruses.

Accordingly, the vaccine composition of the invention may have built-in cross-species and/or cross-genus efficacy, i.e. be a cross-protective vaccine composition. Thus, a single flavivirus vaccine composition of the invention may be used to confer protection against a variety of different flaviviruses. This provides a cost-effective means of controlling the spread of flavivirus infection. A single vaccine composition of the invention may be used to confer protection against one or more different flaviviruses and one or more other viruses, such as Chikungunya virus. This provides a cost-effective means of controlling the spread of mosquito-borne infections.

Inclusion of conserved peptides in the vaccine composition may confer protective capability against emerging flavivirus strains associated with rapid evolution of the flavivirus genome. This may assist in the long-term control of the flavivirus infection.

Inclusion of a flavivirus peptide comprising a conserved CD8+ T cell epitope in the vaccine composition of the invention may beneficially prevent or minimise the development of antibody-dependent enhancement of Dengue virus infection following administration of the vaccine composition.

Interaction with HLA Supertypes

The vaccine composition may comprise at least two flavivirus peptides comprising a CD8+ T cell epitope which each interacts with a different HLA supertype. Including a plurality of such peptides in the vaccine composition allows the vaccine composition to elicit a CD8+ T cell response in a greater proportion of individuals to which the vaccine composition is administered. This is because the vaccine composition should be capable of eliciting a CD8+ T cell response in all individuals of an HLA supertype that interacts with one of the CD8+ T cell epitopes comprised in the plurality of flavivirus peptides. Each CD8+ T cell epitope may interact with HLA-A1, HLA-A2, HLA-A3, HLA-A24, HLA-B7, HLA-B8, HLA-B27, HLA-B44, HLA-B58 or HLA-B62, or any other HLA supertype know in the art. Any combination of flavivirus peptides comprising such a CD8+ T cell epitope is possible. For example, the vaccine composition may comprise two or more of (i) a flavivirus peptide which interacts with HLA-A2, (ii) a flavivirus peptide which interacts with HLA-A3, (iii) a flavivirus peptide which interacts with HLA-A24, and (iv) a flavivirus peptide which interacts with HLA-B7. The vaccine composition may comprise (i) and (ii); (i) and (iii); (i) and (iv); (ii) and (iii); (ii) and (iv); (iii) and (iv); (i), (ii) and (iii); (i), (ii) and (iv); (i), (iii) and (iv); (ii), (iii) and (iv); or (i), (ii), (iii) and (iv).

The vaccine composition may comprise at least one flavivirus peptide comprising a CD8+ T cell epitope which interacts at least two different HLA supertypes. Again, this allows the vaccine composition to elicit a CD8+ T cell response in a greater proportion of individuals to which the vaccine composition is administered. The vaccine composition may comprise at least two, at least three, at least four, at least five, at least two, at least fifteen, or at least twenty flavivirus peptides comprising a CD8+ T cell epitope that each interact with at least two different HLA subtypes. Each flavivirus peptide may interact with at least two, at least three, at least four, at least five, at least six, at least 7, at least 8, at least 9 or at least 10 different HLA supertypes. Each flavivirus peptide may interact with two or more of HLA-A1, HLA-A2, HLA-A3, HLA-A24, HLA-B7, HLA-B8, HLA-B27, HLA-B44, HLA-B58 or HLA-B62, or any other HLA supertype known in the art, in any combination. For example, each flavivirus peptide may interact with two or more of (i) HLA-A2, (ii) HLA-A3, (iii) HLA-A24, and (iv) HLA-B7. Each flavivirus peptide may interact with (i) and (ii); (i) and (iii); (i) and (iv); (ii) and (iii); (ii) and (iv); (iii) and (iv); (i), (ii) and (iii); (i), (ii) and (iv); (i), (iii) and (iv); (ii), (iii) and (iv); or (i), (ii), (iii) and (iv).

Preferably, the vaccine composition comprises a flavivirus peptide comprising a CD8+ T cell epitope that interacts with HLA-A2 and HLA-24. In this case, the vaccine composition may, for example, comprise a flavivirus peptide comprising a CD8+ T cell set out in SEQ ID NO: 1, 2, 6, 12, 13 15, 16, 17, 19 or 20.

Preferably, the vaccine composition comprises a flavivirus peptide comprising a CD8+ T cell epitope that interacts with HLA-A2, HLA-A3 and HLA-24. In this case, the vaccine composition may, for example, comprise a flavivirus peptide comprising a CD8+ T cell set out in SEQ ID NO: 19 or 20.

CD4+ T Cell Epitopes

The vaccine composition of the invention may comprise a peptide comprising a CD4+ T cell epitope. The vaccine composition may comprise two or more, such as three or more, four or more, five our more, ten or more, fifteen or more or twenty or more peptides comprising a CD4+ T cell epitope. A CD4+ T cell epitope is a peptide that is capable of (i) presentation by a class II MHC molecule and (ii) recognition by a T cell receptor (TCR) present on a CD4+ T cell. Preferably, recognition by the TCR results in activation of the CD4+ T cell. CD4+ T cell activation may lead to increased proliferation and/or cytokine production.

The CD4+ T cell epitope may be a flavivirus CD4+ T cell epitope. That is, the CD4+ T cell epitope may be a peptide that is expressed by one or more flaviviruses and that is that is capable of (i) presentation by a class II MHC molecule and (ii) recognition by a T cell receptor (TCR) present on a CD4+ T cell. Such peptides are known in the art.

The CD4+ T cell epitope may be a CD4+ T cell epitope other than a flavivirus CD4+ T cell epitope. For example, the CD4+ T cell may be expressed by an organism other than a flavivirus. The CD4+ T cell epitope may, for example, be expressed by *Clostriudium tetani*. For instance, the CD4+ T cell epitope may be derived from tetanus toxin.

The CD4+ T cell epitope may be a CD4+ T cell epitope that reacts with all class II HLA types, i.e. a so-called "promiscuous" epitope. Inclusion of a promiscuous epitope in the vaccine composition may improve the ability of the vaccine composition to induce an immune response to the flavivirus peptide comprising one or more of the CD8+ T cell epitopes set out in SEQ ID NOs: 1 to 23 or a variant thereof. The CD4+ T cell epitope may, for example, comprise the sequence FKLQTMVKLFNRIKNNVA (SEQ ID NO: 24) and/or the sequence LQTMVKLFNRIKNNVAGGC (SEQ ID NO: 25). SEQ ID NOs 24 and 25 are promiscuous epitopes derived from tetanus toxin.

The peptide comprising a CD4+ T cell epitope may be a different peptide from the flavivirus peptide comprising one or more of the CD8+ T cell epitopes set out in SEQ ID NOs: 1 to 23 or a variant thereof. The CD4+ T cell epitope may, for instance, be comprised in an additional peptide in the vaccine composition, i.e. in a peptide that does not comprise one or more of the CD8+ T cell epitopes set out in SEQ ID NOs: 1 to 23 or a variant thereof. As mentioned above, the additional peptide may comprise one or more CD8+ T cell epitopes and/or one or more B cell epitopes as well as the CD4+ T cell epitope. For instance, the additional peptide may comprise one or more flavivirus CD8+ T cell epitopes.

The peptide comprising a CD4+ T cell epitope may be the same peptide as the flavivirus peptide comprising one or more of the CD8+ T cell epitopes set out in SEQ ID NOs: 1 to 23 or a variant thereof. That is, the flavivirus peptide comprising one or more of the CD8+ T cell epitopes set out in SEQ ID NOs: 1 to 23 or a variant thereof may further comprise a CD4+ T cell epitope.

When the peptide comprising a CD4+ T cell epitope also comprises a CD8+ T cell epitope (such as one or more of the CD8+ T cell epitopes set out in SEQ ID NOs: 1 to 23 or a variant thereof), the CD8+ epitope may be nested within the CD4+ T cell epitope. CD4+ T cell epitopes are typically longer than CD8+ T cell epitopes. Therefore, extending one or both termini of the CD8+ T cell epitope may yield a longer, CD4+ T cell epitope whose sequence still comprises the CD8+ T cell epitope. Therefore, the CD4+ T cell epitope may comprise a CD8+ T cell epitope, such as a CD8+ T cell epitope set out in SEQ ID NOs: 1 to 23 or a variant thereof, extended at its N-terminus or C-terminus. The CD8+ T cell epitope may be extended by 1, 2, 3, 4 or 5 amino acids at its N terminus. The CD8+ T cell epitope may be extended by 1, 2, 3, 4 or 5 amino acids at its C terminus. Preferably, the CD8+ T cell epitope is extended by 3 amino acids at the N terminus, and 3 amino acids at the C terminus. However, the CD8+ T cell epitope need not be extended by the same number of amino acids at each terminus.

The CD8+ T cell epitope nested within a CD4+ T cell epitope may be capable of generating a robust CTL response. The extended peptide (CD4+ T cell epitope) may be capable of inducing T helper mediated cytokine responses. Thus, inclusion of a flavivirus peptide comprising a CD8+ T cell epitope and a CD4+ T cell epitope in the vaccine composition may allow the vaccine composition to induce both cytotoxic and helper T cell responses.

The flavivirus peptide comprising a CD4+ T cell epitope may be attached to a nanoparticle. When the peptide comprising a CD4+ T cell epitope is a different peptide from the flavivirus peptide comprising one or more of the CD8+ T cell epitopes set out in SEQ ID NOs: 1 to 23 or a variant thereof, each peptide may be attached to the same nanoparticle or to a different nanoparticle. The nanoparticle may be a gold nanoparticle. Nanoparticles and attachment thereto are described below.

B Cell Epitopes

The vaccine composition of the invention may comprise a peptide comprising a B cell epitope. The vaccine composition may comprise two or more, such as three or more, four or more, five our more, ten or more, fifteen or more or twenty or more peptides comprising a B cell epitope. A B cell epitope is a peptide that is capable of recognition by a B cell receptor (BCR) present on a B cell. Preferably, recognition by the BCR results in activation and/or maturation of the B cell. B cell activation may lead to increased proliferation, and/or antibody production.

The B cell epitope may be a flavivirus CD4+ T cell epitope. That is, the B cell epitope may be a peptide that is expressed by one or more flaviviruses and that is capable of recognition by a B cell receptor (BCR) present on a B cell. Such peptides are known in the art.

The B cell epitope may be a linear epitope, i.e. an epitope that is defined by the primary amino acid sequence of a particular region of a filovirus protein. Alternatively, the epitope may be a conformational epitope, i.e. an epitope that is defined by the conformational structure of a native flavivirus protein. In this case, the epitope may be continuous (i.e. the components that interact with the antibody are situated next to each other sequentially on the protein) or discontinuous (i.e. the components that interact with the antibody are situated on disparate parts of the protein, which are brought close to each other in the folded native protein structure).

Typically, the B cell epitope is around 5 to 20 amino acids in length, such as 6 to 19, 7 to 18, 8 to 17, 9 to 16, 10 to 15, 11 to 14 or 12 to 13 amino acids in length.

Methods for identifying B cell epitopes are also known in the art. For instance, epitope mapping methods may be used to identify B cell epitopes. These methods include structural approaches, wherein the known or modelled structure of a protein is be used in an algorithm based approach to predict surface epitopes, and functional approaches, wherein the binding of whole proteins, protein fragments or peptides to an antibody can be quantitated e.g. using an Enzyme-Linked Immunosorbent Assay (ELISA). Competition mapping, antigen modification or protein fragmentation methods may also be used.

Nanoparticles

In the vaccine composition of the invention, the flavivirus peptide comprising one or more of the CD8+ T cell epitopes set out in SEQ ID NOs: 1 to 23 or a variant thereof may be attached to a nanoparticle. Any other peptides further comprised in the vaccine composition may also be attached to a nanoparticle. Attachment to a nanoparticle, for example a gold nanoparticle, is beneficial.

As set out above and demonstrated in the Examples below, attachment of the peptide to a nanoparticle (such as a gold nanoparticle) reduces or eliminates the need to include a virus or an adjuvant in the vaccine composition. The nanoparticles may contain immune "danger signals" that help to effectively induce an immune response to the peptides. The nanoparticles may induce dendritic cell (DC) activation and maturation, required for a robust immune response. The nanoparticles may contain non-self components that improve uptake of the nanoparticles and thus the peptides by cells, such as antigen presenting cells. Attachment of a peptide to a nanoparticle may therefore enhance the ability of antigen presenting cells to stimulate virus-specific T and/or B cells. Attachment to a nanoparticle also facilitates delivery of the vaccine compositions via the subcutaneous, intradermal, transdermal and oral/buccal routes, providing flexibility in administration.

Nanoparticles are particles between 1 and 100 nanometers (nm) in size which can be used as a substrate for immobilising ligands. In the vaccine compositions of the invention, the nanoparticle may have a mean diameter of 1 to 100, 20 to 90, 30 to 80, 40 to 70 or 50 to 60 nm. Preferably, the nanoparticle has a mean diameter of 20 to 40 nm. A mean diameter of 20 to 40 nm facilitates uptake of the nanoparticle to the cytosol. The mean diameter can be measured using techniques well known in the art such as transmission electron microscopy.

Nanoparticles suitable for the delivery of antigen, such as a flavivirus peptide, are known in the art. Methods for the production of such nanoparticles are also known.

The nanoparticle may, for example, be a polymeric nanoparticle, an inorganic nanoparticle, a liposome, an immune stimulating complex (ISCOM), a virus-like particle (VLP), or a self-assembling protein. The nanoparticle is preferably a calcium phosphate nanoparticle, a silicon nanoparticle or a gold nanoparticle.

The nanoparticle may be a polymeric nanoparticle. The polymeric nanoparticle may comprise one or more synthetic polymers, such as poly(d,l-lactide-co-glycolide) (PLG), poly(d,l-lactic-coglycolic acid) (PLGA), poly(g-glutamic acid) (g-PGA)m poly(ethylene glycol) (PEG), or polystyrene. The polymeric nanoparticle may comprise one or more natural polymers such as a polysaccharide, for example pullulan, alginate, inulin, and chitosan. The use of a polymeric nanoparticle may be advantageous due to the properties of the polymers that may be include in the nanoparticle. For instance, the natural and synthetic polymers recited above may have good biocompatibility and biodegradability, a non-toxic nature and/or the ability to be manipulated into desired shapes and sizes. The polymeric nanoparticle may form a hydrogel nanoparticle. Hydrogel nanoparticles are a type of nano-sized hydrophilic three-dimensional polymer network. Hydrogel nanoparticles have favourable properties including flexible mesh size, large surface area for multivalent conjugation, high water content, and high loading capacity for antigens. Polymers such as Poly(L-lactic acid) (PLA), PLGA, PEG, and polysaccharides are particularly suitable for forming hydrogel nanoparticles.

The nanoparticle may be an inorganic nanoparticle. Typically, inorganic nanoparticles have a rigid structure and are non-biodegradable. However, the inorganic nanoparticle may be biodegradable. The inorganic nanoparticle may comprise a shell in which an antigen may be encapsulated. The inorganic nanoparticle may comprise a core to which an antigen may be covalently attached. The core may comprise a metal. For example, the core may comprise gold (Au), silver (Ag) or copper (Cu) atoms. The core may be formed of more than one type of atom. For instance, the core may comprise an alloy, such as an alloy of Au/Ag, Au/Cu, Au/Ag/Cu, Au/Pt, Au/Pd or Au/Ag/Cu/Pd. The core may comprise calcium phosphate (CaP). The core may comprise a semiconductor material, for example cadmium selenide.

Other exemplary inorganic nanoparticles include carbon nanoparticles and silica-based nanoparticles. Carbon nanoparticles are have good biocompatibility and can be synthesized into nanotubes and mesoporous spheres. Silica-based nanoparticles (SiNPs) are biocompatible and can be prepared with tunable structural parameters to suit their therapeutic application.

The nanoparticle may be a silicon nanoparticle, such as an elemental silicon nanoparticle. The nanoparticle may be mesoporous or have a honeycomb pore structure. Preferably, the nanoparticle is an elemental silicon particle having a honeycomb pore structure. Such nanoparticles are known in the art and offer tunable and controlled drug loading, targeting and release that can be tailored to almost any load, route of administration, target or release profile. For example, such nanoparticles may increase the bioavailability of their load, and/or improve the intestinal permeability and absorption of orally administered actives. The nanoparticles may have an exceptionally high loading capacity due to their porous structure and large surface area. The nanoparticles may release their load over days, weeks or months, depending on their physical properties. Since silicon is a naturally occurring element of the human body, the nanoparticles may elicit no response from the immune system. This is advantageous to the in vivo safety of the nanoparticles.

Any of the SiNPs described above may be biodegradable or non-biodegradable. A biodegradable SiNP may dissolve to orthosilic acid, the bioavailable form of silicon. Orthosilic acid has been shown to be beneficial for the health of bones, connective tissue, hair, and skin.

The nanoparticle may be a liposome. Liposomes are typically formed from biodegradable, non-toxic phospholipids and comprise a self-assembling phospholipid bilayer shell with an aqueous core. A liposome may be an unilameller vesicle comprising a single phospholipid bilayer, or a multilameller vesicle that comprises several concentric phospholipid shells separated by layers of water. As a consequence, liposomes can be tailored to incorporate either hydrophilic molecules into the aqueous core or hydrophobic molecules within the phospholipid bilayers. Liposomes may encapsulate antigen within the core for delivery. Liposomes may incorporate viral envelope glycoproteins to the shell to form virosomes. A number of liposome-based products are established in the art and are approved for human use.

The nanoparticle may be an immune-stimulating complex (ISCOM). ISCOMs are cage-like particles which are typically formed from colloidal saponin-containing micelles. ISCOMs may comprise cholesterol, phospholipid (such as phosphatidylethanolamine or phosphatidylcholine) and saponin (such as Quil A from the tree *Quillaia saponaria*). ISCOMs have traditionally been used to entrap viral envelope proteins, such as envelope proteins from herpes simplex virus type 1, hepatitis B, or influenza virus.

The nanoparticle may be a virus-like particle (VLP). VLPs are self-assembling nanoparticles that lack infectious nucleic acid, which are formed by self-assembly of biocompatible capsid protein. VLPs are typically about 20 to about 150 nm, such as about 20 to about 40 nm, about 30 to about 140 nm, about 40 to about 130 nm, about 50 to about 120 nm, about 60 to about 110 nm, about 70 to about 100 nm, or about 80 to about 90 nm in diameter. VLPs advantageously harness the power of evolved viral structure, which is naturally optimized for interaction with the immune system. The naturally-optimized nanoparticle size and repetitive structural order means that VLPs induce potent immune responses, even in the absence of adjuvant.

The nanoparticle may be a self-assembling protein. For instance, the nanoparticle may comprise ferritin. Ferritin is a protein that can self-assemble into nearly-spherical 10 nm structures. The nanoparticle may comprise major vault protein (MVP). Ninety-six units of MVP can self-assemble into a barrel-shaped vault nanoparticle, with a size of approximately 40 nm wide and 70 nm long.

The nanoparticle may be a calcium phosphate (CaP) nanoparticle. CaP nanoparticles may comprise a core comprising one or more (such as two or more, 10 or more, 20 or more, 50 or more, 100 or more, 200 or more, or 500 or more) molecules of CaP. CaP nanoparticles and methods for their production are known in the art. For instance, a stable nano-suspension of CAP nanoparticles may be generated by mixing inorganic salt solutions of calcium and phosphates in pre-determined ratios under constant mixing.

The CaP nanoparticle may have an average particle size of about 80 to about 100 nm, such as about 82 to about 98 nm, about 84 to about 96 nm, about 86 to about 94 nm, or about 88 to about 92 nm. This particle size may produce a better performance in terms of immune cell uptake and immune response than other, larger particle sizes. The particle size may be stable (i.e. show no significant change), for instance when measured over a period of 1 month, 2 months, 3 months, 6 months, 12 months, 18 months, 24 months, 36 months or 48 months.

CaP nanoparticles can be co-formulated with one or multiple antigens either adsorbed on the surface of the nanoparticle or co-precipitated with CaP during particle synthesis. For example, a peptide, such as a flavivirus peptide, may be attached to the CaP nanoparticle by dissolving the peptide in DMSO (for example at a concentration of about 10 mg/ml), adding to a suspension of CaP nanoparticles together with N-acetyl-glucosamine (GlcNAc) (for example at 0.093 mol/L and ultra-pure water, and mixing at room temperature for a period of about 4 hours (for example, 1 hour, 2 hours, 3 hours, 5 hours, 6 hours, 7 hours, 8 hours, 9 hours or 10 hours).

The vaccine composition may comprise about 0.15 to about 0.8%, such as 0.2 to about 0.75%, 0.25 to about 0.7%, 0.3 to about 0.6%, 0.35 to about 0.65%, 0.4 to about 0.6%, or 0.45 to about 0.55%, CaP nanoparticles. Preferably the vaccine composition comprises about 0.3% CaP nanoparticles.

CaP nanoparticles have a high degree of biocompatibility due to their chemical similarity to human hard tissues such as bone and teeth. Advantageously, therefore, CaP nanoparticles are non-toxic when used for therapeutic applications. CaP nanoparticles are safe for administration via intramuscular, subcutaneous, oral, or inhalation routes. CaP nanoparticles are also simple to synthesise commercially. Furthermore, CaP nanoparticles may be associated with slow release of antigen, which may enhance the induction of an immune response to a peptide attached to the nanoparticle. CaP nanoparticles may be used both as an adjuvant, and as a drug delivery vehicle.

The nanoparticle may be a gold nanoparticle. Gold nanoparticles are known in the art and are described in particular in WO 2002/32404, WO 2006/037979, WO 2007/122388, WO 2007/015105 and WO 2013/034726. The gold nanoparticle attached to each peptide may be a gold nanoparticle described in any of WO 2002/32404, WO 2006/037979, WO 2007/122388, WO 2007/015105 and WO 2013/034726.

Gold nanoparticles comprise a core comprising a gold (Au) atom. The core may further comprise one or more Fe, Cu or Gd atoms. The core may be formed from a gold alloy, such as Au/Fe, Au/Cu, Au/Gd, Au/Fe/Cu, Au/Fe/Gd or Au/Fe/Cu/Gd. The total number of atoms in the core may be 100 to 500 atoms, such as 150 to 450, 200 to 400 or 250 to 350 atoms. The gold nanoparticle may have a mean diameter of 1 to 100, 20 to 90, 30 to 80, 40 to 70 or 50 to 60 nm. Preferably, the gold nanoparticle has a mean diameter of 20 to 40 nm.

The nanoparticle may comprise a surface coated with alpha-galactose and/or beta-GlcNHAc. For instance, the nanoparticle may comprise a surface passivated with alpha-galactose and/or beta-GlcNHAc. In this case, the nanoparticle may, for example, be a nanoparticle which comprises a core including metal and/or semiconductor atoms. For instance, the nanoparticle may be a gold nanoparticle. Beta-GlcNHAc is a bacterial pathogen-associated-molecular pattern (PAMP), which is capable of activating antigen-presenting cells. In this way, a nanoparticle comprising a surface coated or passivated with Beta-GlcNHAc may non-specifically stimulate an immune response. Attachment of the flavivirus peptide comprising one or more of the CD8+ T cell epitopes set out in SEQ ID NOs: 1 to 23 or a variant thereof to such a nanoparticle may therefore improve the immune response elicited by administration of the vaccine composition of the invention to an individual.

One or more ligands other than the peptide may be linked to the nanoparticle, which may be any of the types of nanoparticle described above. The ligands may form a "corona", a layer or coating which may partially or completely cover the surface of the core. The corona may be considered to be an organic layer that surrounds or partially surrounds the nanoparticle core. The corona may provide or participate in passivating the core of the nanoparticle. Thus, in certain cases the corona may be a sufficiently complete coating layer to stabilise the core. The corona may facilitate solubility, such as water solubility, of the nanoparticles of the present invention.

The nanoparticle may comprise at least 10, at least 20, at least 30, at least 40 or at least 50 ligands. The ligands may include one or more peptides, protein domains, nucleic acid molecules, lipidic groups, carbohydrate groups, anionic groups, or cationic groups, glycolipids and/or glycoproteins. The carbohydrate group may be a polysaccharide, an oligosaccharide or a monosaccharide group (e.g. glucose). One or more of the ligands may be a non-self component, that renders the nanoparticle more likely to be taken up by antigen presenting cells due to its similarity to a pathogenic component. For instance, one or more ligands may comprise a carbohydrate moiety (such as a bacterial carbohydrate moiety), a surfactant moiety and/or a glutathione moiety. Exemplary ligands include glucose, N-acetylglucosamine (GlcNAc), glutathione, 2'-thioethyl-3-D-glucopyranoside and 2'-thioethyl-D-glucopyranoside. Preferred ligands include glycoconjugates, which form glyconanoparticles Linkage of the ligands to the core may be facilitated by a linker. The linker may comprise a thiol group, an alkyl group, a glycol group or a peptide group. For instance, the linker may comprise C2-C15 alkyl and/or C2-C15 glycol. The linker may comprise a sulphur-containing group, amino-containing group, phosphate-containing group or oxygen-containing group that is capable of covalent attachment to the core. Alternatively, the ligands may be directly linked to the core, for example via a sulphur-containing group, amino-containing group, phosphate-containing group or oxygen-containing group comprised in the ligand.

Attachment to Nanoparticles

The peptide may be attached at its N-terminus to the nanoparticle. Typically, the peptide is attached to the core of the nanoparticle, but attachment to the corona or a ligand may also be possible.

The peptide may be directly attached to the nanoparticle, for example by covalent bonding of an atom in a sulphur-containing group, amino-containing group, phosphate-containing group or oxygen-containing group in the peptide to an atom in the nanoparticle or its core.

A linker may be used to link the peptide to the nanoparticle. The linker may comprise a sulphur-containing group, amino-containing group, phosphate-containing group or oxygen-containing group that is capable of covalent attachment to an atom in the core. For example, the linker may comprise a thiol group, an alkyl group, a glycol group or a peptide group.

The linker may comprise a peptide portion and a non-peptide portion. The peptide portion may comprise the sequence $X_1X_2Z_1$, wherein $X_1$ is an amino acid selected from A and G; $X_2$ is an amino acid selected from A and G; and $Z_1$ is an amino acid selected from Y and F. The peptide portion may comprise the sequence AAY or FLAAY. The peptide portion of the linker may be linked to the N-terminus of the peptide. The non-peptide portion of the linker may comprise a C2-C15 alkyl and/a C2-C15 glycol, for example a thioethyl group or a thiopropyl group.

The linker may be (i) HS—$(CH_2)_2$—CONH-AAY; (ii) HS—$(CH_2)_2$—CONH-LAAY; (iii) HS—$(CH_2)_3$—CONH-AAY; (iv) HS—$(CH_2)_3$—CONH-FLAAY; (v) HS—$(CH_2)_{10}$—$(CH_2OCH_2)_7$—CONH-AAY; and (vi) HS—$(CH_2)_{10}$—$(CH_2OCH_2)_7$—CONH-FLAAY. In this case, the thiol group of the non-peptide portion of the linker links the linker to the core.

Other suitable linkers for attaching a peptide to a nanoparticle are known in the art, and may be readily identified and implemented by the skilled person.

As explained above, the vaccine composition may comprise multiple flavivirus peptides each comprising one or more of the CD8+ T cell epitopes set out in SEQ ID NOs: 1 to 9. The vaccine composition may comprise one or more additional peptides each comprising an epitope, such as a CD4+ T cell epitope, a B cell epitope, or a CD8+ T cell epitope other than the CD8+ T cell epitopes set out in SEQ ID NOs: 1 to 9. Thus, the vaccine composition may comprise more than one peptide.

When the vaccine composition comprises more than one peptide, two or more (such as three or more, four or more, five or more, ten or more, or twenty or more) of the peptides may be attached to the same nanoparticle. Two or more (such as three or more, four or more, five or more, ten or more, or twenty or more) of the peptides may each be attached to different nanoparticle. The nanoparticles to which the peptides are attached may though be the same type of nanoparticle. For instance, each peptide may be attached to a gold nanoparticle. Each peptide may be attached to a CaP nanoparticle. The nanoparticle to which the peptides are attached may be a different type of nanoparticle. For instance, one peptide may be attached to a gold nanoparticle, and another peptide may be attached to a CaP nanoparticle.

Polynucleotide Vaccines

The invention provides a vaccine composition comprising a polynucleotide encoding a flavivirus peptide comprising one or more of the CD8+ T cell epitopes set out in SEQ ID NOs: 1 to 23 or a variant thereof. The advantageous properties of such polynucleotide vaccines are described above.

The vaccine composition may comprise a polynucleotide encoding two or more flavivirus peptides each comprising a different CD8+ T cell epitope. The vaccine composition may comprise two or more polynucleotides each encoding a flavivirus peptide comprising a different CD8+ T cell epitope. In either case, each flavivirus peptide may comprise a peptide set out in SEQ ID NOs: 1 to 23 or a variant thereof.

Flavivirus peptides, CD8+ T cell epitopes and variants are described in detail above in connection with the peptide vaccine of the invention. Any of the aspects described in connection with the peptide vaccine may apply to the polynucleotide vaccine.

The polynucleotide may be DNA. The polynucleotide may be RNA. For example, the polynucleotide may be mRNA. In other words, the polynucleotide may be a RNA polynucleotide that is complementary to a DNA polynucleotide encoding encoding a flavivirus peptide comprising one or more of the CD8+ T cell epitopes set out in SEQ ID NOs: 1 to 23 or a variant thereof.

Medicaments, Methods of Treatment and Therapeutic Use

The invention provides a method of preventing or treating a flavivirus infection, comprising administering the vaccine composition of the invention to an individual infected with, or at risk of being infected with, a flavivirus. The invention also provides a vaccine composition of the invention for use in a method of preventing or treating a flavivirus infection in an individual.

The flavivirus infection may be, for example, a Zika virus infection, a Dengue virus infection, a West Nile virus infection, a yellow fever virus infection, a St. Louis encephalitis virus infection, a Japanese encephalitis virus infection, a Murray Valley encephalitis virus infection, a Tick-borne encephalitis virus infection, a Kunjin encephalitis virus infection, a Rocio encephalitis virus infection, a Russian Spring Summer encephalitis virus infection, Negeishi virus infection, a Kyasanur Forest infection, a Omsk Hemorrhagic Fever virus infection, a Powassan virus infection, a Louping Ill virus infection, a Rio Bravo virus infection, a Tyuleniy virus infection, a Ntaya virus infection or a Modoc virus infection. The Zika virus infection may, for example, be African Zika Virus infection or Asian Zika Virus infection. The Dengue virus may, for example, be DENV-1 infection, DENV-2 infection, DENV-3 infection or DENV-4 infection.

The vaccine composition may be provided as a pharmaceutical composition. The pharmaceutical composition preferably comprises a pharmaceutically acceptable carrier or diluent. The pharmaceutical composition may be formulated using any suitable method. Formulation of cells with standard pharmaceutically acceptable carriers and/or excipients may be carried out using routine methods in the pharmaceutical art. The exact nature of a formulation will depend upon several factors including the cells to be administered and the desired route of administration. Suitable types of formulation are fully described in Remington's Pharmaceutical Sciences, 19th Edition, Mack Publishing Company, Eastern Pennsylvania, USA.

The vaccine composition or pharmaceutical composition may be administered by any route. Suitable routes include, but are not limited to, the intravenous, intramuscular, intraperitoneal, subcutaneous, intradermal, transdermal and oral/buccal routes.

Compositions may be prepared together with a physiologically acceptable carrier or diluent. Typically, such compositions are prepared as liquid suspensions of peptides and/or peptide-linked nanoparticles. The peptides and/or peptide-linked nanoparticles may be mixed with an excipient which is pharmaceutically acceptable and compatible with the active ingredient. Suitable excipients are, for example, water, saline, dextrose, glycerol, of the like and combinations thereof.

In addition, if desired, the pharmaceutical compositions may contain minor amounts of auxiliary substances such as wetting or emulsifying agents, and/or pH buffering agents.

The peptides or peptide-linked nanoparticles are administered in a manner compatible with the dosage formulation and in such amount will be therapeutically effective. The quantity to be administered depends on the subject to be treated, the disease to be treated, and the capacity of the subject's immune system. Precise amounts of nanoparticles required to be administered may depend on the judgement of the practitioner and may be peculiar to each subject.

Any suitable number of peptides or peptide-linked nanoparticles may be administered to a subject. For example, at least, or about, $0.2\times10^6$, $0.25\times10^6$, $0.5\times10^6$, $1.5\times10^6$, $4.0\times10^6$ or $5.0\times10^6$ peptides or peptide-linked nanoparticles per kg of patient may administered. For example, at least, or about, $10^5$, $10^6$, $10^7$, $10^8$, $10^9$ peptides or peptide-linked nanoparticles may be administered. As a guide, the number of peptides or peptide-linked nanoparticles to be administered may be from $10^5$ to $10^9$, preferably from $10^6$ to $10^8$.

Methods

The invention provides a method for generating cytotoxic T lymphocytes (CTLs) for use in passive immunotherapy, comprising contacting T cells obtained from a subject infected with a flavivirus with a flavivirus peptide comprising one or more of the CD8+ T cell epitopes set out in SEQ ID NOs: 1 to 23 or a variant thereof.

The term "passive immunotherapy" relates to the administration of immune system components (such as immune cells) to an individual to aid in the treatment of a disease. The disease may be an infection. The infection may be a flavivirus infection, such as a Zika virus infection, a Dengue virus infection, a West Nile virus infection, a yellow fever virus infection, a St. Louis encephalitis virus infection, a Japanese encephalitis virus infection, a Murray Valley encephalitis virus infection, a Tick-borne encephalitis virus infection, a Kunjin encephalitis virus infection, a Rocio encephalitis virus infection, a Russian Spring Summer encephalitis virus infection, Negeishi virus infection, a Kyasanur Forest infection, a Omsk Hemorrhagic Fever virus infection, a Powassan virus infection, a Louping Ill virus infection, a Rio Bravo virus infection, a Tyuleniy virus infection, a Ntaya virus infection or a Modoc virus infection. The Zika virus infection may, for example, be African Zika Virus infection or Asian Zika Virus infection. The Dengue virus may, for example, be DENV-1 infection, DENV-2 infection, DENV-3 infection or DENV-4 infection.

Flavivirus peptides, CD8+ T cell epitopes and variants are described in detail above in connection with the peptide vaccine of the invention. Any of the aspects relating to flavivirus peptides, CD8+ T cell epitopes and variants described in connection with the peptide vaccine may apply to the method for generating CTLs.

The method may be performed in vitro or ex vivo. The contacting step may be performed in vitro or ex vivo.

The T cells obtained from the subject may comprise CD8+ T cells. The T cells obtained from the subject may comprise CD8+ T cells and CD4+ T cells.

The subject from which the T cells are obtained may also be the recipient of the CTLs produced by the method. That is, the subject from which the T cells are obtained may be treated with the CTLs produced by the method. In this case, the CTLs are autologous to the recipient of the CTLs.

The subject from which the T cells are obtained may be a different individual from the recipient of the CTLs produced by the method. In other words, the T cells may be obtained from a donor and used in the method, and the resultant CTLs administered to a different individual. Accordingly, the CTLs may be allogeneic with respect to the recipient of the CTLs.

The subject from which the T cells are obtained may be HLA-matched with the recipient of the CTLs produced by the method. In other words, the T cells may be obtained from a donor and used in the method, and the resultant CTLs administered to an HLA-matched individual. Accordingly, the CTLs may be HLA-matched with respect to the recipient of the CTLs.

The invention further provides a method for diagnosing a flavivirus infection in a subject, comprising (i) contacting T cells obtained from the subject with a flavivirus peptide comprising one or more of the CD8+ T cell epitopes set out in SEQ ID NOs: 1 to 23 or a variant thereof and (ii) determining the response of the T cells to the flavivirus peptide.

The flavivirus infection may, for example, be a Zika virus infection, a Dengue virus infection, a West Nile virus infection, a yellow fever virus infection, a St. Louis encephalitis virus infection, a Japanese encephalitis virus infection, a Murray Valley encephalitis virus infection, a Tick-borne encephalitis virus infection, a Kunjin encephalitis virus infection, a Rocio encephalitis virus infection, a Russian Spring Summer encephalitis virus infection, Negeishi virus infection, a Kyasanur Forest infection, a Omsk Hemorrhagic Fever virus infection, a Powassan virus infection, a Louping Ill virus infection, a Rio Bravo virus infection, a Tyuleniy virus infection, a Ntaya virus infection or a Modoc virus infection. The Zika virus infection may, for example, be African Zika Virus infection or Asian Zika Virus infection. The Dengue virus may, for example, be DENV-1 infection, DENV-2 infection, DENV-3 infection or DENV-4 infection.

Step (i) of the method may be performed in vitro or ex vivo. The T cells may be CD4+ T cells, CD8+ T cells, or a mixture of CD4+ T cells and CD8+ T cells. Preferably, the T cells are CD8+ T cells. In step (i), the T cells may be contacted with one flavivirus peptide comprising one or more of the CD8+ T cell epitopes set out in SEQ ID NOs: 1 to 23 or a variant thereof. The T cells may be contacted with two or more flavivirus peptides each comprising one or more of the CD8+ T cell epitopes set out in SEQ ID NOs: 1 to 23 or a variant thereof, in any combination. Flavivirus peptides, CD8+ T cell epitopes and variants are described in detail above in connection with the peptide vaccine of the invention. Any of the aspects relating to flavivirus peptides, CD8+ T cell epitopes and variants described in connection with the peptide vaccine may apply to the method for diagnosing a flavivirus infection.

Mechanisms for determining the response of T cells to contact with a peptide are known in the art. Any such mechanism may be used in step (ii) of the method to determine the response of the T cells to the flavivirus peptide. The response may, for example, be proliferation of T cells. T cell proliferation may, for example, be determined by measuring the incorporation of tritiated thymidine, dilution of intracellular dyes such as CFSE (carboxyfluorescein succinimidyl ester), or using fluorescent or colorimetic indicators of metabolic activity such as alamarBlue. The response may, for example, be activation of T cells. Markers of activated T cells are well-known in the art. Marker expression may be determined using flow cytometry or immunofluorescent imaging. The response may, for example, be cytokine expression. Cytokine expression may be determined using flow cytometry, immunofluorescent imaging or an ELISA (enzyme-linked immunosorbent assay), for example. Expression of other immune system mediators such as perforin or granzyme may similarly be determined.

Further Aspects of the Invention

Further aspects of the invention include:

1. An isolated oligopeptide or peptide in a pharmaceutical composition comprising at least one peptide having an amino acid sequence selected from the group consisting of SEQ ID NO: 1 to 14, said oligopeptide or peptide consisting of 8 to about 30 amino acid residues, wherein said oligopeptide or peptide binds to class I MHC molecules or can be processed to bind to class I MHC molecules and activate T lymphocyte response and wherein the oligopeptide or peptide is in the form of a pharmaceutically acceptable salt.

2. The oligopeptide of aspect 1 wherein said oligopeptide comprises at least two epitopic peptides.

3. The oligopeptide of aspect 1 wherein said oligopeptide comprises at least three epitopic peptides.

4. The oligopeptide of aspect 1 wherein said oligopeptide comprises at least four epitopic peptides.

5. The oligopeptide or peptide of aspect 1 wherein said oligopeptide or peptide differs from SEQ ID NO: 1, 2, 3, 4, 5, 6, 7, 8, 9, 10, 11, 12 13 or 14 wherein said difference is no more than one amino acid unit.

6. The oligopeptide or peptide of aspect 5 wherein said one amino acid difference is the result of a conservative amino acid substitution.

7. The oligopeptide or peptide of aspect 5 wherein said one amino acid difference is the substitution of one hydrophobic amino acid with another hydrophobic amino acid.

8. The oligopeptide or peptide of aspect 5 wherein said amino acid difference is the addition or deletion of one amino acid to or from said epitopic peptide.

9. A polynucleotide in a pharmaceutical composition comprising a polynucleotide selected from the group consisting of: (a) a polynucleotide that encodes an oligopeptide or peptide of aspect 1, and (b) the full complement of (a) wherein the polynucleotide is in a form of a pharmaceutically acceptable salt.

10. The polynucleotide of aspect 9 wherein the polynucleotide of (a) is DNA.

11. The polynucleotide of aspect 9 wherein the polynucleotide of (a) is RNA.

12. A method for vaccinating and treating a subject for any flavivirus infection, said infected cells expressing any class IMHC molecule, comprising administering to said subject a composition that binds to class I MHC molecules or can be processed to bind to class I MHC molecules comprising: at least one polypeptide comprising an epitopic peptide comprising an amino acid sequence selected from the group consisting of SEQ ID NO: 1 to 14 in an amount sufficient to induce a CTL response to said infected cells and in a form of a pharmaceutically acceptable salt; or at least one polypeptide comprising an epitopic peptide having at least one amino acid difference from an amino acid sequence selected from the group consisting of SEQ ID NO: 1 to 14 in an amount sufficient to induce a CTL response to said infected cells and in a form of a pharmaceutically acceptable salt.

13. A method for vaccinating and treating a subject with any flavivirus infection, said infected cells expressing any class I MHC molecule, said method comprising administering to said subject a composition that binds to class I MHC molecules or can be processed to bind to class I MHC molecules comprising: a polynucleotide comprising a nucleic acid sequence encoding at least one polypeptide comprising an amino acid sequence selected from the group consisting of SEQ ID NO: 1 to 14 in an amount sufficient to induce a CTL response to said infected cells and in a form of a pharmaceutically acceptable salt; or at least one polypeptide comprising an epitopic peptide comprising one amino acid difference from an amino acid sequence selected from the group consisting of SEQ ID NO: 1 to 14 in an amount sufficient to induce a CTL response to said infected cells and in a form of a pharmaceutically acceptable salt.

14. A method for generating an immune response ex vivo using T cells from a subject infected with any flavivirus, said method comprising: stimulating the production of CTL response for use in passive immunotherapy, wherein said T cells react with at least one polypeptide comprising an amino acid sequence selected from the group consisting of SEQ ID NO: 1 to 14 and in a form of a pharmaceutically acceptable salt; or at least one polypeptide comprising one amino acid difference from an amino acid sequence selected from the group consisting of SEQ ID NO: 1 to 14 and in a form of a pharmaceutically acceptable salt.

15. The method of aspect 14, wherein said T cell adoptive therapy generated from autologous or HLA matched subjects.

16. A method for assessing or diagnosing an immune response in a subject infected with any flavivirus or vaccinated for any flavivirus and related viruses said method comprising: stimulating the production of CTL response, wherein said T cells react with at least one polypeptide comprising an amino acid sequence selected from the group consisting of SEQ ID NO: 1 to 14 and in a form of a pharmaceutically acceptable salt; or at least one polypeptide comprising one amino acid difference from an amino acid sequence selected from the group consisting of SEQ ID NO: 1 to 14 and in a form of a pharmaceutically acceptable salt.

17. A method for vaccinating humans against any flavivirus infection using SEQ IDs 1 to 14 in a form of a pharmaceutically acceptable salt.

It is to be understood that different applications of the disclosed products and methods may be tailored to the specific needs in the art. It is also to be understood that the terminology used herein is for the purpose of describing particular embodiments of the invention only, and is not intended to be limiting.

In addition, as used in this specification and the appended claims, the singular forms “a”, “an”, and “the” include plural referents unless the content clearly dictates otherwise. Thus, for example, reference to “a peptide” includes “peptides”, reference to “a nanoparticle” includes two or more such nanoparticles, and the like.

All publications, patents and patent applications cited herein, whether supra or infra, are hereby incorporated by reference in their entirety.

The following Examples illustrate the invention.

Example 1

Introduction

ZIKA Virus (ZIKV) is a RNA virus transmitted to humans by *Aedes* mosquitoes. Until recently, it was thought to be relatively harmless with only 20% of infections resulting in mild, short-lived symptoms such as rash, headache and conjunctivitis. Recent reports linking the current South American ZIKV outbreak to an increase in the number of microencephalic babies born in Brazil and Guillain-Barre syndrome cases in El Salvador has prompted a reassessment. The severity of these conditions increase drug industry interest in vaccine development. Efforts could focus on modification of vaccines for related diseases. The Flavivirus is closely related to Dengue. Flavivirus is a member of the Flaviviridae family, which includes dengue fever, yellow fever, Japanese encephalitis, tick-borne encephalitis, and West Nile viruses. Presently there is no vaccine or specific treatment for ZIKV.

Dengue (1-3) and Chikungunya are global infections priorities in their own right with Dengue infecting 390 million people per year, and Chikungunya having intermittent high profile outbreaks. Zika, Dengue and Chikungunya are spread by the same type of mosquito in the same lower/middle income regions and therefore a vaccine consisting shared T cell epitopes will be able to provide triple protection against all three infections and would provide a practical and logical benefit.

Dengue, Zika and Chikungunya viruses are all carried by the same mosquito and there is considerable clinical overlap between the three (FIG. 1A). They all share similar viral protein arrangements. It has been experimentally confirmed that there are sufficient cross-reactive epitopes between the three viruses such that a triple vaccine against Dengue, Zika and Chikungunya can be produced.

Human Flavivirus infection occurs when a blood-feeding female *Aedes* mosquito deposits the virus into human skin and the blood stream. Both human epidermal keratinocytes and dermal fibroblasts are permissive to flavivirus infection. The expression of pathogen recognition receptor (PRR)s, toll-like receptor (TLR), RIG-1 and MDA-5, which subsequently trigger the expression of type 1-IFNs, IFN stimulated genes, including OAS2, ISG-15 and MX-1, and inflammatory cytokines are upregulated by infection of dermal fibroblasts with Flavivirus. Type 1- and 2-IFNs are known to be important for control of all flaviviruses infections. Both types of IFNs inhibit replication of Flavivirus in human fibroblasts. The role of these cytokines in host-defense mechanisms is further confirmed in murine model, in which mice deficient in the type 1-IFN receptor (A129) or type 1- and type 2-IFN receptors (AG129) are highly susceptible to Flavivirus infection, with viremia and age-dependent mortality. Serological analysis of patients with Flavivirus disease demonstrated both anti-ZIKV-virus IgG and IgM and neutralizing antibodies, which were demonstrated to provide partial protection in infant and adult mice against lethal Flavivirus infection.

Neutralizing antibodies provide partial protection, whereas type 1- and type 2-IFNs are important in controlling Flavivirus infection (4). Transmission of Flavivirus in humans is demonstrated via blood transfusion, sexual intercourse and perinatal transmission from mother to fetus at the time of delivery, in addition to the mosquito transmission. Thus, identifying immune factors that lead to viral clearance in periphery will provide significant visions into the development of immunotherapy and vaccines against the Flavivirus infection (5).

The advantage of flavivirus vaccine programs is that they can use similar mosquito-based diseases, part of a family called flaviviruses, like dengue, West Nile virus, and chikungunya as a “jumping off” point. While researchers are currently trying to learn more about the basics of the Flavivirus and its effects on the human body given how new the disease is, they can already use past vaccine development platforms from other flaviviruses as a foundation since they spread in similar ways. NIAID is actively pursuing multiple vaccine candidates to prevent Flavivirus infection, including: a DNA-based vaccine, similar to a strategy used for West Nile virus, which has been found safe and effective in a phase one trial. It is also working on a more traditional live virus-vaccine, similar to those already developed to prevent dengue, an investigational ZIKV vaccine that uses a genetically engineered version of vesicular stomatitis virus, an animal virus that primarily affects cattle, and a whole-particle inactivated ZIKV vaccine based on a similar vaccine approach used by the Walter Reed Army Institute of Research (WRAIR) to develop vaccines against the related Japanese Encephalitis and dengue viruses. It is possible that an investigational ZIKV vaccine will be ready to enter early-stage human trials in the fall of 2016. An early-stage trial would examine whether an experimental vaccine is safe and generates immune responses in vaccinated volunteers. A safe and effective, fully licensed ZIKV vaccine will likely not be available for several years.

Specifically, the ZIKV epidemic is primarily a fetal-maternal issue (6), given the lasting impact of congenital Zika virus syndrome on the health of a population. Evidence has confirmed a link between ZIKV infections in pregnant mothers and birth defects (i.e. microcephaly, intracranial lesions, vision problems, hearing loss) (7, 8). It is also now proposed that in 20% of cases maternal ZIKV can lead to some form of neurologic damage to the fetus. In order to have an effective vaccination regime to combat the main fetal related pathological features of the ZIKV outbreak, a vaccine that is able to vaccinate both the mother and the fetus simultaneously is required. Most current vaccine technologies are not suited to in utero vaccination (9-18). Antibody vaccines are not suited since antibodies cannot cross the placenta until late pregnancy so ZIKV related pathology that occurs in the fetus in 1st/2nd trimester will not be diminished by maternal antibodies. A vaccine that promotes a T-cell response in the mother cannot protect the fetus, since maternal CD8+ CTL cells are destroyed by the placenta via the HLA-G system (14, 15). Any fetal or maternal microchimerism is also suppressed by fetal T regs (16). An attenuated live virus would be able to pass to the fetus and provoke an immune response (the fetus is immunologically competent ~10 weeks), but it may not be appropriate from a safety perspective to expose the fetus to live virus (9-18). Furthermore, there will always be a brief viremia phase (no vaccine is considered complete) even if the mother is pre-immunized against ZIKV, meaning the fetus will always be at risk of infection. A purely synthetic vaccine that is capable of generating a T cell immune response that eliminates the infected cells in the mother and reduces the prolonged viremia and more importantly, vaccinate the fetus, would have the potential to reduce the birth defects in the fetus. A vaccine of this nature has some important qualities that make it compatible with in utero vaccination.

Supporting Data

Our approach to T-cell epitope discovery is based on the premise that the immune system can mount an effective response to specific antigens expressed on diseased, but not healthy cells. The immunoproteomics methodology directly isolates MHC-associated peptides from infected cells and identifies epitopes (authentic T cell targets) as they are presented on the surface of the diseased cell. Using this technical approach, we have identified T-cell epitopes from, ZIKV, Dengue, HBV-, and influenza-virus-infected cells as well as various cancer indications.

Flavivirus Epitopes Identified from Infected Cells by Immunoproteomics Analysis

For our initial discovery phase, we used HLA-A2 and A24 positive HepG2 cells for infection. ZIKV was acquired from ATCC (ATCC #1839) and propagated through infection of Vero cells for 72 hours. Dengue virus was obtained from Walter Reed research institute and propagated using Vero cells infection. At 72 hours post infection (hpi) the viral titers from the supernatant was characterized by plaque assay. HepG2 cells were infected at a MOI of 0.1 for 72 hours. The infected HepG2 cells were harvested and assessed for infectivity by permeabilizing and staining with anti-flavivirus group antigen (anti-4G2 MAb; MAB10216, Millipore) antibody and analyzed by flow cytometry. The infected cells were processed further for immunoproteomics analysis as described elsewhere (19-21). Briefly, cell lysates were prepared from the infected cells and MHC/peptide complexes were isolated by immunoprecipitation using a pan MHC class I antibody, W632. Then, peptides associated with the MHC molecules were isolated and purified using analytical methods. The purified peptide mixture was fractionated using an offline HPLC and the fractions were analyzed by data dependent nano LC-MS/MS experiments on an Velos LTQ-Orbitrap mass spectrometer (Thermo Fisher) interfaced with a nano ultimate HPLC (Dionex). MHC peptides and their sequences were identified by searching the LC-MS/MS raw data against ZIKV genome databases using proteome discoverer software (v 1.3) with Sequest search algorithm (Thermo). In addition, the data was searched against other flaviviruses, dengue and chikungunya genome databases. Immunoproteomics analysis of ZIKV infected cells resulted in identification of several T cell epitopes (Table 4). Most of the epitopes were HLA-A2 or A2/A24 dual HLA binding epitopes, as we have seen in our dengue vaccine studies (19). In addition, we identified B7 and B44 binding epitopes from various ZIKV proteins. Most importantly, we identified several epitopes that are conserved across ZIKV, dengue and Chikungunya virus. These epitopes were derived from the conserved regions of the viral genome, which may be responsible for survival in the host mosquito. These epitopes were further confirmed by synthetic peptide co-elution experiments (FIG. 2—PMA peptide (Table 4) spectra obtained from experimental and synthetic peptide mass spec analysis and FIGS. 3A and 3B—FLM peptide (Table 4) spectra obtained from experimental and synthetic peptide mass spec analysis).

TABLE 4

| Peptide ID | HLA motif | Virus Specificity | Access ID | Protein |
|---|---|---|---|---|
| IAVAVSSAIL | A2 | Dengue/ZIKV | B3U3M3 | NS4B, Zika & Dengue |
| PMAAVGLLIVS | A2/A24 | Dengue/ZIKV | Q32ZE1 | NS2B, Zika & Dengue |
| WVTDHSGKTV | A2 | Dengue/ZIKV/ West Nile | A0A096XFQ2 | HELICc, Zika & Dengue |
| LVERGYLQ | A2 | Dengue/ZIKV/ HIV | A0A096XFQ2 | FtsJ-like methyltransferase, Zika |
| 1MLLGLLGTV | A2 | ZIKV | Q32ZE1 | NS4A |
| ALGLTAVRLV DPI | A2/A24 | ZIKV | B3U3M3 | E protein, transmembrane |
| DESRAKVEVTP NSPR | B44 | ZIKV | W8PAE0 | Envelope glycoprotein |
| DPAVIGTAVK | B7 | ZIKV | Q32ZE1 | NS1 |
| WPPSEVLTAVG | B7 | ZIKV | Q32ZE1 | NS2 |
| DIGAVALDYPA | A24 | ZIKV | Q32ZE1 | Peptidase S7, Flavivirus NS3 serine protease |
| EWEKRIAEAI | A24 | Dengue/CHIK | gi296124571 | non-structural polyprotein [Chikungunya virus] |
| FILLSMVGIAA | A2/24 | Dengue/CHIK | gi538281039 | envelope protein 2, partial [Chikungunya virus] |
| FLMCKTTDMV | A2/24 | Dengue/CHIK | gi288572690 | non-structural polyprotein [Chikungunya virus] |
| LQAVMAVPDT | A2 | Dengue/CHIK | gi81951234 | non-structural polyprotein [Chikungunya virus] |

REFERENCES

1. Rothman A L. Dengue: defining protective versus pathologic immunity. The Journal of clinical investigation. 2004; 113(7):946-51. Epub 2004/04/02. doi: 10.1172/JCI21512. PubMed PMID: 15057297; PubMed Central PMCID: PMC379334.
2. Weiskopf D. Sette A. T-cell immunity to infection with dengue virus in humans. Frontiers in immunology. 2014; 5:93. Epub 2014/03/19. doi: 10.3389/fimmu.2014.00093. PubMed PMID: 24639680; PubMed Central PMCID: PMC3945531.
3. Khan A M, Miotto O, Nascimento E J, Srinivasan K N, Heiny A T, Zhang G L. et al. Conservation and variability of dengue virus proteins: implications for vaccine design. PLoS neglected tropical diseases. 2008; 2(8):e272. Epub 2008/08/14. doi: 10.1371/joumal.pntd. 0000272. PubMed PMID: 18698358; PubMed Central PMCID: PMC2491585.

4. Hamel R, Dejamac O, Wichit S, Ekchariyawat P, Neyret A, Luplertlop N, et al. Biology of Zika Virus Infection in Human Skin Cells. Journal of virology. 2015; 89(17): 8880-96. Epub 2015/06/19. doi: 10.1128/JVI.00354-15. PubMed PMID: 26085147; PubM^d Central PMCID: PMC4524089.
5. Cheepsattayakom A C R. ika Virus Infection and Disease. J Hum Virol & Retrovirol 2016; 3(2):82. Epub Feb. 17, 2016.
6. Meaney-Delman D, Rasmussen S A, Staples J E, Oduyebo T, Ellington S R, Petersen E E, et al. Zika Virus and Pregnancy: What Obstetric Health Care Providers Need to Know. Obstetrics and gynecology. 2016; 127(4): 642-8. Epub 2016/02/19. doi: 10.1097/AOG.0000000000001378. PubMed PMID: 26889662.
7. Rasmussen S A, Jamieson D J, Honein M A, Petersen L R. Zika Virus and Birth Defects-Reviewing the Evidence for Causality. The New England journal of medicine. 2016; 374(20):1981-7. Epub 2016/04/14. doi: 10.1056/NEJMsr 1604338. PubMed PMID: 27074377.
8. Calvet G, Aguiar R S. Melo A S, Sampaio S A, de Filippis I, Fabri A, et al. Detection and sequencing of Zika virus from amniotic fluid of fetuses with microcephaly in Brazil: a case study. The Lancet Infectious diseases. 2016; 16(6):653-60. Epub 2016/02/22. doi: 10.1016/81473-3099(16)00095-5. PubMed PMID: 26897108.
9. Chavant F, Ingrand I, Jonville-Bera A P, Plazanet C, Gras-Champel V, Lagarce L, et al. The PREGVAXGRIP study: a cohort study to assess foetal and neonatal consequences of in utero exposure to vaccination against A(HlN1)v2009 influenza. Drug safety. 2013; 36(6):455-65. Epub 2013/03/22. doi: 10.1007/s40264-013-0030-1. PubMed PMID: 23516007.
10. Conlin A M, Bukowinski A T, Sevick C J, DeScisciolo C, Crum-Cianflone N F. Safety of the pandemic H1N1 influenza vaccine among pregnant U.S. military women and their newborns. Obstetrics and gynecology. 2013; 121(3):511-8. Epub 2013/05/03. doi: 10.1097/AOG.0b013e318280d64e. PubMed PMID: 23635612.
11. Kaposy C, Lafferty L. Overcoming liability concerns in vaccine trials involving pregnant women. Accountability in research. 2012; 19(3):156-74. Epub 2012/06/13. doi: 10.1080/08989621.2012.678686. PubMed PMID: 22686632.
12. Vanderbeeken Y, Sarfati M, Bose R, Delespesse G. In utero immunization of the fetus to tetanus by maternal vaccination during pregnancy. American journal of reproductive immunology and microbiology: AJRIM. 1985; 8(2):39-42. Epub 1985/06/01. PubMed PMID: 4025666.
13. Marchant A, Appay V, Van Der Sande M, Dulphy N, Liesnard C, Kidd M, et al. Mature CD8(+) T lymphocyte response to viral infection during fetal life. The Journal of clinical investigation. 2003; 111(11):1747-55. Epub 2003/06/05. doi: 10.1172/JCI17470. PubMed PMID: 12782677; PubMed Central PMCID: PMC 156108.
14. Hunt J S, Petroff M G, McIntire R H, Ober C. HLA-G and immune tolerance in pregnancy. FASEB journal: official publication of the Federation of American Societies for Experimental Biology. 2005; 19(7):681-93. Epub 2005/04/29. doi: 10.1096/fj.04-2078rev. PubMed PMID: 15857883.
15. Le Bouteiller P. HLA-G in human early pregnancy: control of uterine immune cell activation and likely vascular remodeling. Biomedical journal. 2015; 38(1):32-8. Epub 2014/08/29. doi: 10.4103/2319-4170.131376. PubMed PMID: 25163504.
16. Mold J E, Michaelsson J, Burt T D, Muench M O, Beckerman K P, Busch M P, et al. Maternal alloantigens promote the development of tolerogenic fetal regulatory T cells in utero. Science. 2008; 322(5907): 1562-5. Epub 2008/12/06. doi: 10.1126/science. 1164511. PubMed PMID: 19056990; PubMed Central PMCID: PMC2648820.
17. Rastogi D, Wang C, Mao X, Lendor C, Rothman P B. Miller R L. Antigen-specific immune responses to influenza vaccine in utero. The Journal of clinical investigation. 2007; 117(6):1637-46. Epub 2007/06/06. doi: 10.1172/JCI29466. PubMed PMID: 17549258: PubMed Central PMCID: PMC1878514.
18. Hermann E, Truyens C, Alonso-Vega C, Even J, Rodriguez P, Berthe A, et al. Human fetuses are able to mount an adultlike CDS T-cell response. Blood. 2002; 100(6): 2153-8. Epub 2002/08/30. PubMed PMID: 12200380.
19. Testa J S, Shetty V, Sinnathamby G. Nickens Z, Hafner J, Kamal S, et al. Conserved MHC class I-presented dengue virus epitopes identified by immunoproteomics analysis are targets for cross-serotype reactive T-cell response. J Infect Dis. 2012; 205(4):647-55. Epub 2012/01/17. doi: 10.1093/infdis/jir814. PubMed PMID: 22246683.
20. Testa J S, Shetty V, Hafner J, Nickens Z, Kamal S, Sinnathamby G, et al. MHC class I-presented T cell epitopes identified by immunoproteomics analysis are targets for a cross reactive influenza-specific T cell response. PLoS One. 2012; 7(1 1):e48484. Epub 2012/11/13. doi: 10.1371/journal.pone.0048484. PubMed PMID: 23144892; PubMed Central PMCID: PMC3492461.
21. Comber J D, Karabudak A, Shetty V, Testa J S, Huang X, Philip R. MHC Class I Presented T Cell Epitopes as Potential Antigens for Therapeutic Vaccine against HBV Chronic Infection. Hepatitis research andtreatment. 2014; 2014:860562. Epub 2014/06/28. doi: 10.1155/2014/860562. PubMed PMID: 24971174; PubMed Central PMCID: PMC4058288.

Example 2

Introduction

The concept of “universal” vaccines that cover an entire genus is dependent on the generation of identical or cross-reactive class I viral epitopes expressed on the surface of viral infected cells (in contrast to the surface antigens of virions themselves that are the targets for antibodies). These peptide targets are independent of the recognition of the intact virus (as required for antibody-based vaccines) and in general they are derived from processed class I peptides from internal proteins of the virus during its synthesis in the host cell. The peptides generated by the immuno-ribosome or Defective Ribosomal Product (DRiP) pathway can come from proteins that are present in all members of a genus. For example, the flavivirus genus contains 66 members including Dengue, Zika, Yellow fever etc. and all of these viral strains have internal proteins in common (with significant homology) that give rise to an extensive cross-reactive peptide ligandome signature (target for CD8 T cells) on host infected cells. High stability and favourable production timescales/economics means these vaccines are perfectly suited as an on-demand practical solution to Dengue/Flavivirus outbreaks.

In order to develop a vaccine against all strains of Dengue, CD8 T cells must be expanded from naive clones that target the class I viral signature on a host Dengue infected cells. These class I complexes are the targets for the CD8 T cell to kill the infected cell via recognition of the cognate T cell receptor (TCR). T cell vaccines are considered "sterilizing" vaccines in contrast to the antibody vaccines that can only reduce viremia and then leave it to the host immune system to clear the viral factory cells using CD8 cytotoxic T cells. In a natural infection the ligandome information is transferred from the remote infected cell to the immune system (i.e. antigen presenting cells (APCs)) in lymphoid organs, skin etc. via exosomes. These particles deliver the peptide information to the APC that then activate naive T cells. This is a pure information transfer system. In order to mimic this process with a vaccine you need to know the viral signature (i.e. ligandome) of the infected cell. Once you have that information it needs to be delivered to the immune system by some form of artificial exosomes. The term "vaccine" is used herein in a generic sense to imply an agent that is able to change the initial immunological conditions present at the time of a viral infection. Vaccine candidates described herein use quantum clusters to deliver the class I peptides directly to APC via lymphatic uptake of specialized particles that both protect the peptides from degradation during transit to the APCs, and allow cytoplasmic release of the intact class I peptides for incorporation into class I structures on the surface of the APC in order to activate naive T cells. No other vaccine company has been able to solve this series of technical hurdles. At present, attempts to produce universal vaccines are dependent, in general, on the introduction into a host cell of a viral protein which then is hopefully processed to give rise to class I peptides. This methodology may not work because of the law of mass action. At any given time, only 100,000 class I molecules are expressed on a human cell. However, there are millions of possible class I binding peptides that can be derived from all of the host proteins. All of these will be competing for a binding site on the 100,00 class I molecules. In a viral infected cell, a separate processing pathway is used to generate class I peptides that represent the viral signature such that they are not "swamped" by all of the internal peptides. For the viral vaccines that attempt to generate class I peptides by vectors these proteins are process as if they are host proteins and thus any peptides generated get diluted and have little chance of appearing on the surface of the transfected cell. Further these cells do not in general release vast amounts of exosomes to deliver the peptide fragments to remote APC (in contrast viral infected cells are fragile and release lots of debris). This is at least one reason for the failure of previous attempts to develop experimental universal vaccines. Further, in general only one/two of the viral proteins can be delivered to a host cell in a single viral vector or RNA package and thus experimental ligandome knowledge is required to know if peptides generated from the viral expressed protein actual ever appear as part of the cell ligandome. Since these vaccines are being developed without knowledge of experimental determined ligandomes they will have a high failure rate.

1. Technical Summary 1.1 Vaccine Design and Peptide Selection Strategy

Using an immunoproteomics approach, MHC-class I viral peptides from the conserved regions of the Flavivirus have been identified. Briefly, a human cell of a predefined human HLA supertype is infected with a Flavivirus (i.e. Dengue or Zika) and the peptides expressed on the surface of that cell are extracted and identified using mass spectrometry. The protein origin of extracted and identified peptides can be assigned to be derived from either viral proteins or endogenous (i.e. human) proteins (self). The MHC-1 peptides associated with infection can be confirmed and this library of identified MHC-1 peptides is the repertoire of peptides that the T-cell immune system will recognise as an infectious signal—leading to killing of the infected cell expressing these peptides expressed in its class I molecules. The ligandome is the complete set of structures in which a natural immune response can be derived. Therefore, those peptides can be used as a basis for a vaccination agent to prime the immune system against infection. The set of identified peptides is known as the viral "ligandome". The challenge of vaccine and peptide design is to select the peptides from the "ligandome" library that will form a final clinical vaccine candidate and also have a delivery mechanism to educated naive T cells resulting in an immune repertoire of memory T cells similar to one that would occur after a natural infection.

The following are the rational and criteria for selection of such peptides:

1. HLA coverage: Peptides must cover certain HLA supertypes in order to provide appropriate population coverage. In general, 1 HLA supertypes will cover approximately 30-50% of the population, 2 HLA supertypes 70-75% of a population, 3 HLA supertypes will cover approximately 85-95% of the population and 4 HLA types will cover 95%+. For the purposes of the design of this vaccine, a 4 HLA supertype coverage has been selected (HLA-A2/A3/24/B7). The rationale behind this selection is that it is considered an appropriate balance between a reasonable population coverage whilst also limiting the number of peptides required and thus simplifying vaccine design.
2. Multiple protein/peptide coverage: An optimum T-cell vaccine would promote multiple targets of "attack" by the immune system to infected cells via recognition of peptide class I (pMHC). Therefore, it would be advantageous to have multiple peptides for each HLA type. Similarly, having peptides that are derived from a range of viral proteins, which are internal and conserved proteins, would increase the range of infected cell recognition and therefore make the vaccine unsusceptible to antigenic drift and/or shift. RNA viruses such as Dengue are considered "cloud" structures as they are made up of a population of viruses called quasi-species that act in concert to cause disease. Therefore, not every variant will give rise to the same set of class I peptides. Indeed, every mosquito bite inoculation with Dengue into a host is considered a new Founder population of viruses. Multiple simultaneous bites are required to cause disease and create a new population in the infected host. In order to address this issue cross-reactive class peptides, identified in deep sequencing analysis from different genus of flavivirus, provide a high probability of peptides sites that are critical for viral survival and less susceptible to the mutation events that generate lethal consequences (Muller's ratchet). So multiple class I peptides from different proteins should create a T cell repertoire that should reduce bottleneck expansion and thus prevent disease. Our current vaccine candidate will contain 9 peptides as shown in Table 5 below.
3. Ease of manufacture. In general, the more hydrophobic the peptide, the more complex the synthesis and conjugation with the nanoparticle carrier system. Therefore, hydrophilic peptides will be given preference when possible.

Based on the above criteria 9 peptides have been selected to constitute the Dengue (Flavivirus) clinical candidate (Table 5):

TABLE 5

Clinical candidate peptide selection

| Peptide identifier | Sequence | Virus protein | HLA type | Viral origin |
|---|---|---|---|---|
| KLA | KLAEAIFKL | NS5 | A2/24 | DV2 |
| AML | AMLSIPNAII | NS2A | A2/24 | DV2 |
| LLC | LLCVPNIMI | NS2A | A2/A24 | DV2 |
| TIT | TITEEIAVQ | NS4B | A2 | DV2 |
| LVM | LVMKDGRKL | NS5 | A2/3/24 | DV2 |
| LLG | LLGQGPMKLV | Protein C | A2/3/24 | DV2 |
| LMR | LMRNKGIGK | NS4A | A3 | DV2 |
| SPA | SPARLASAI | NS1 | B7 | DV2 |
| APT | APTRVVAAEMEEAL | TBC | B7 | TBC |

1.2 Gold Nanoparticle Carrier

Figure 2:
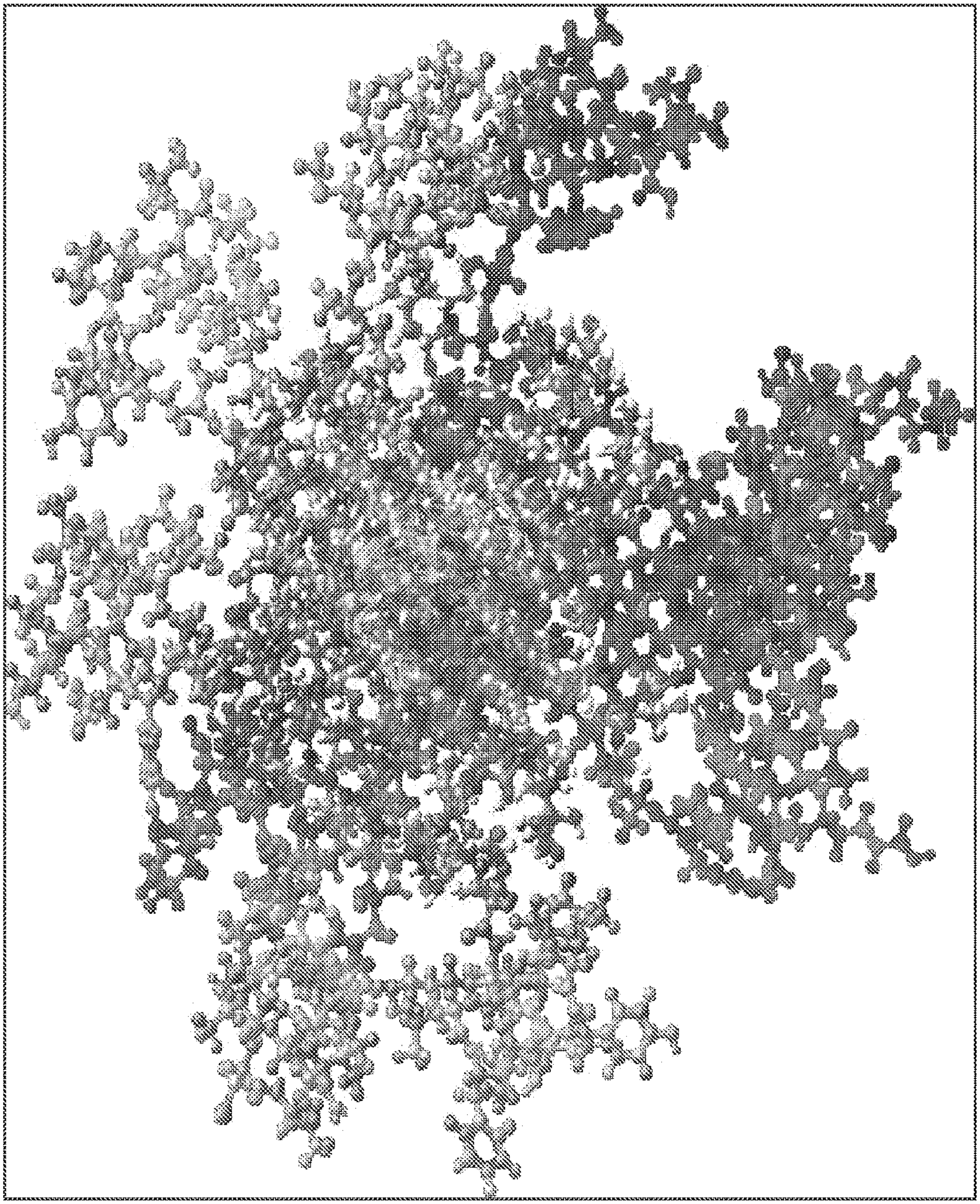
FIG. 2: A totally Synthetic Flavivirus Vaccine. The core is a quantum confined nanocluster passivated with carbohydrate ligands recognized as bacterial pathogen-associated-molecular patterns (PAMPs.). A combination of peptides from the conserved internal vial regions are attached to the surface by linkers which are readily cleaved within the antigen-presenting cell to result in crucial binding to major histocompatibility (MHC) class I molecules. The overall particle is 5 nm in diameter and can be synthesized in a single step reaction using self-assembly supramolecular chemistry.

The final vaccine candidate would be composed of a mixture of gold GNP base particles, each with a Filovirus viral peptide epitope attached to form a GNP-peptide conjugates (FIG. 2). Each particle will have a single particular peptide (as opposed to each nanoparticle having a number of different peptides). The base particle to which the peptides are attached would contain a helper/adjuvant signal by being covered in passivating surface of galactose/GlcNAc. The peptide epitopes would be attached to the base particle via an N terminal AAY-mecaptoacetic acid linker. Once inside antigen presenting cells, this linker is cleaved to release free peptides from the GNP-peptide conjugates. GNP-peptide conjugates widely diffuse from the intra-dermal injection site in human skin, which enables them to bring the attached peptides in contact with epidermal Langerhans cells and dermal dendritic cells. Injection experiments with human skin biopsies have demonstrated that 94% of the residing epidermal Langerhans Cells had taken-up GNP-peptide constructs. This is in contrast to free peptides or peptides complexed with aluminium sulphate which do not diffuse away from the site of injection, and hence have less encounters with antigen presenting cells.

1.3 CTL Assays

As a rule, all ligandome peptides are capable of generating a CTL response, and therefore a quantitative assessment of CTL response for particular peptides is not a decision factor in determining vaccine design. Nevertheless, as a proof of principle, data showing CTL inducing activity of free peptides and peptides bound to the nanoparticle carrier system are included herein. These studies include:

a. Ex vivo: Human blood donated from naive donors (i.e. healthy donors who have not been previously infected by Dengue) are tested for primary immune response to the vaccine constructs. These experiments effectively mimic the process of immunisation at a cellular level and provide proof of mechanism that the experimental vaccines are able to activate naive T cell into antigen specific CD8 cytotoxic T cells that can kill Dengue infected human target cells. These experiments are extended by looking at post-infection memory T-cells using the blood of those previous exposed to infection. If the identified peptides induce a CTL response in post infectious blood (recall response), it illustrates that those are the same MHC-1 peptides that induced a T-cell response in a normal infection. Dendrimer staining also quantifies the number of memory T cells present in a natural infection to peptides to be used in a candidate vaccine.

b. In vivo: Using HLA transgenic mice the ability of the peptides to induce a primary immune response in a biological system has been used. This includes extracting spleen cells from transgenic mice immunised with particular peptide constructs, and assessing CTL activity of those activated cells against peptide target and Dengue infected human cells.

c. It is not possible to do viral challenge studies with human specific HLA vaccines. Whilst humanized mice have a human immune system the target tissues are still murine (they will have mouse MHC rather than human HLA).

1.3.1 In Vitro

Human blood donated from naive donors (i.e. healthy donors who have not been previously infected by Dengue/Zika) was tested for primary immune response to the vaccine constructs. These experiments effectively mimic the process of immunisation at a cellular level and provide proof of mechanism that the experimental vaccines are able to immunise a naive cell. These experiments have been completed for HLA-A2 (FIG. 3A/FIG. 3B) and HLA-A24 (FIG. 4) supertypes.

Figure 3A:
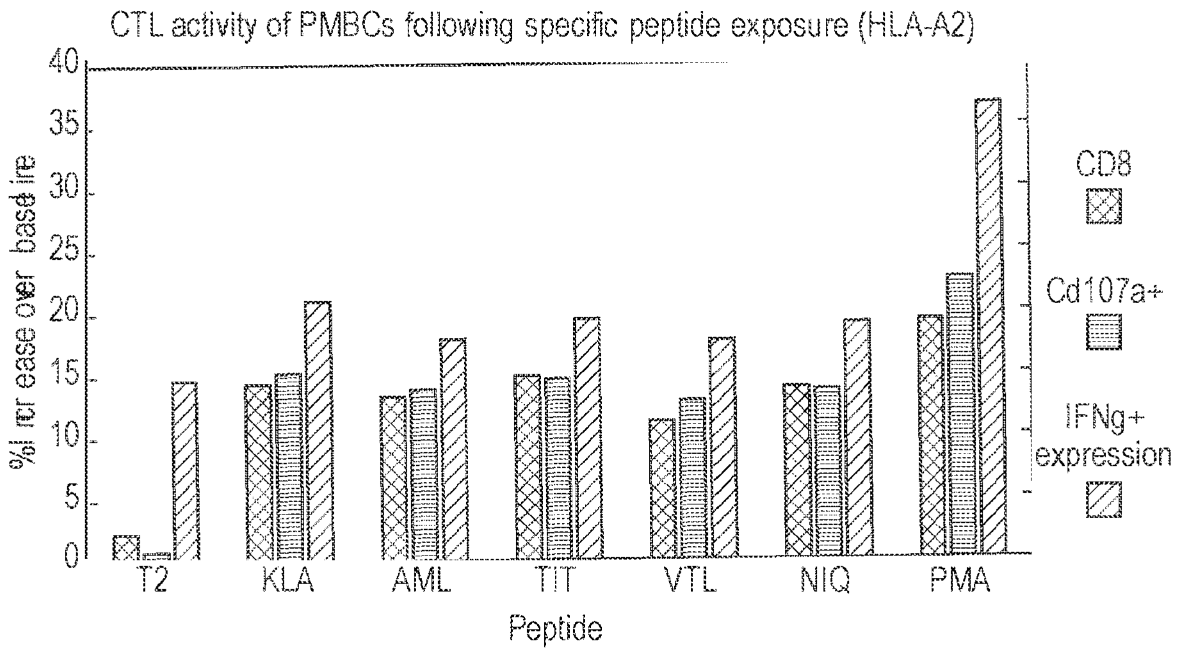
FIGS. 3A and 3B.

In one experiment, utilizing a healthy (naive) human HLA-A2+ donor, peripheral blood mononuclear cells (PBMCs) were stimulated with peptide epitopes in a cytokine cocktail to induce antigen specific CTL response. These stimulated PBMCs were then assayed by co-culturing peptide loaded targets for antigen specific response (FIG. 3A). TAP-deficient cells (T2) were used for peptide loading, and blank T2 cells used as control. Expanded PBMCs were assayed for both CD107a degranulation and interferon gamma (IFN-g) markers by flow cytometry. All 6 peptide epitopes induced CD8+CD107a and IFNg expression to peptide loaded T2 cells in a peptide specific manner. Peptide “PMA” has a particular pronounced IFNg+ effect.

Figure 3B:
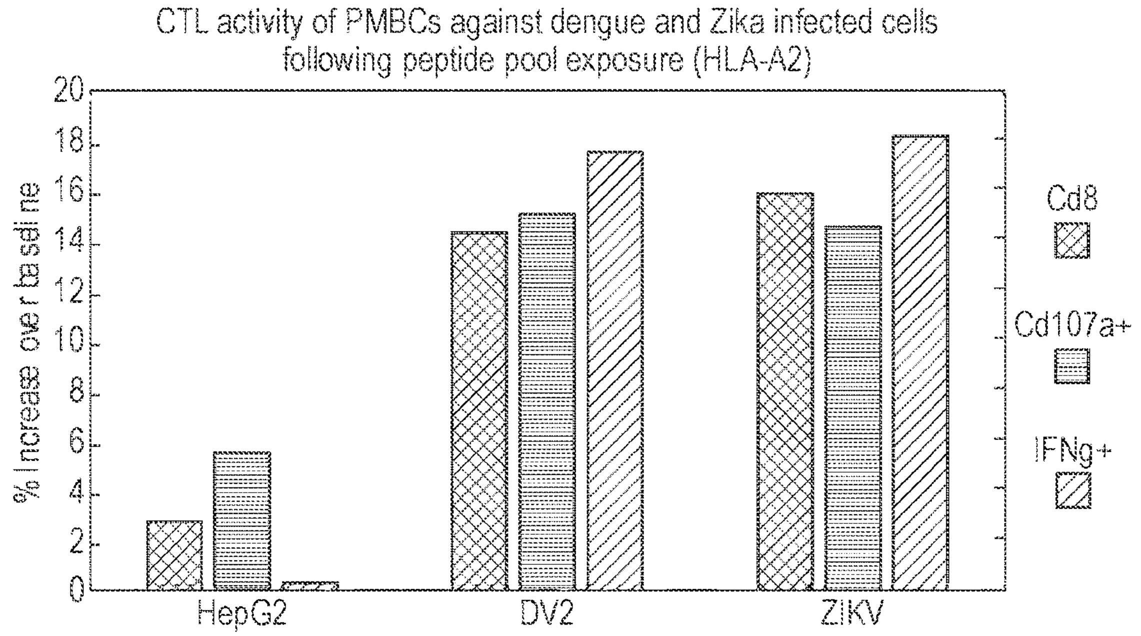

In another experiment, utilizing a healthy (naive) human HLA-A2+ donor, peripheral blood mononuclear cells (PBMCs) were stimulated with peptide epitopes in a cytokine cocktail to induce antigen specific CTL response. These stimulated PBMCs were then assayed by co-culturing with Hep2G infected cells (DV2/Zika) (FIG. 3B). Uninfected HepG2 cells were used as control. Expanded PBMCs were assayed for both CD107a degranulation and interferon gamma (IFN-g) markers by flow cytometry.

Figure 4:
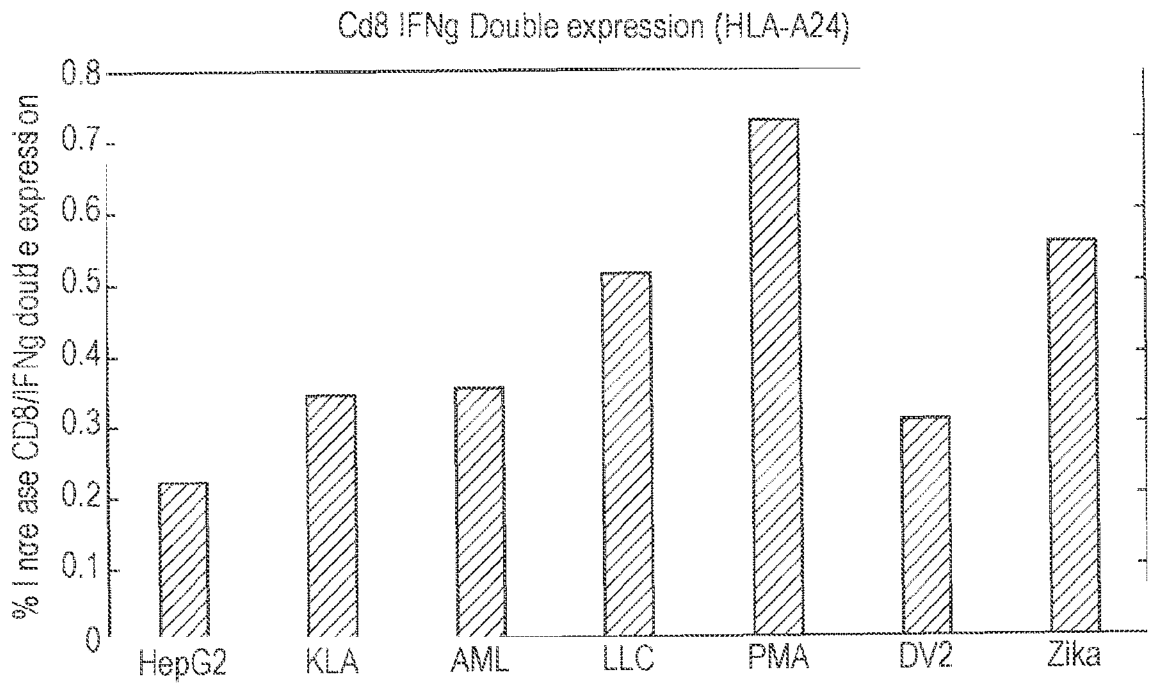
FIG. 4: Utilizing a healthy (naive) human HLA-A24+ donor, peripheral blood mononuclear cells (PBMCs) were stimulated with peptide epitopes in a cytokine cocktail to induce antigen specific CTL response. These stimulated PBMCs were then assayed by co-culturing peptide loaded targets for antigen specific response. Hep2G cells were used for peptide loading, and blank Hep2G cells used as control. Also used was HepG2 cells infected with Dengue (DV2) and Zika. Expanded PBMCs were assayed for both CD8/IFNg double expression by flow cytometry. All 4 peptide epitopes induced CD8+ IFNg expression to peptide loaded HepG2 cells in a peptide specific manner. Peptide "PMA" has a particular pronounced IFNg+ effect.

In a further experiment, utilizing a healthy (naive) human HLA-A24+ donor, peripheral blood mononuclear cells (PBMCs) were stimulated with peptide epitopes in a cytokine cocktail to induce antigen specific CTL response. These stimulated PBMCs were then assayed by co-culturing peptide loaded targets for antigen specific response (FIG. 4). Hep2G cells were used for peptide loading, and blank Hep2G cells used as control. Also used was HepG2 cells infected with Dengue (DV2) and Zika. Expanded PBMCs were assayed for both CD8/IFNg double expression by flow cytometry. All 4 peptide epitopes induced CD8+ IFNg expression to peptide loaded HepG2 cells in a peptide specific manner. Peptide "PMA" has a particular pronounced IFNg+ effect.

Figure 5:
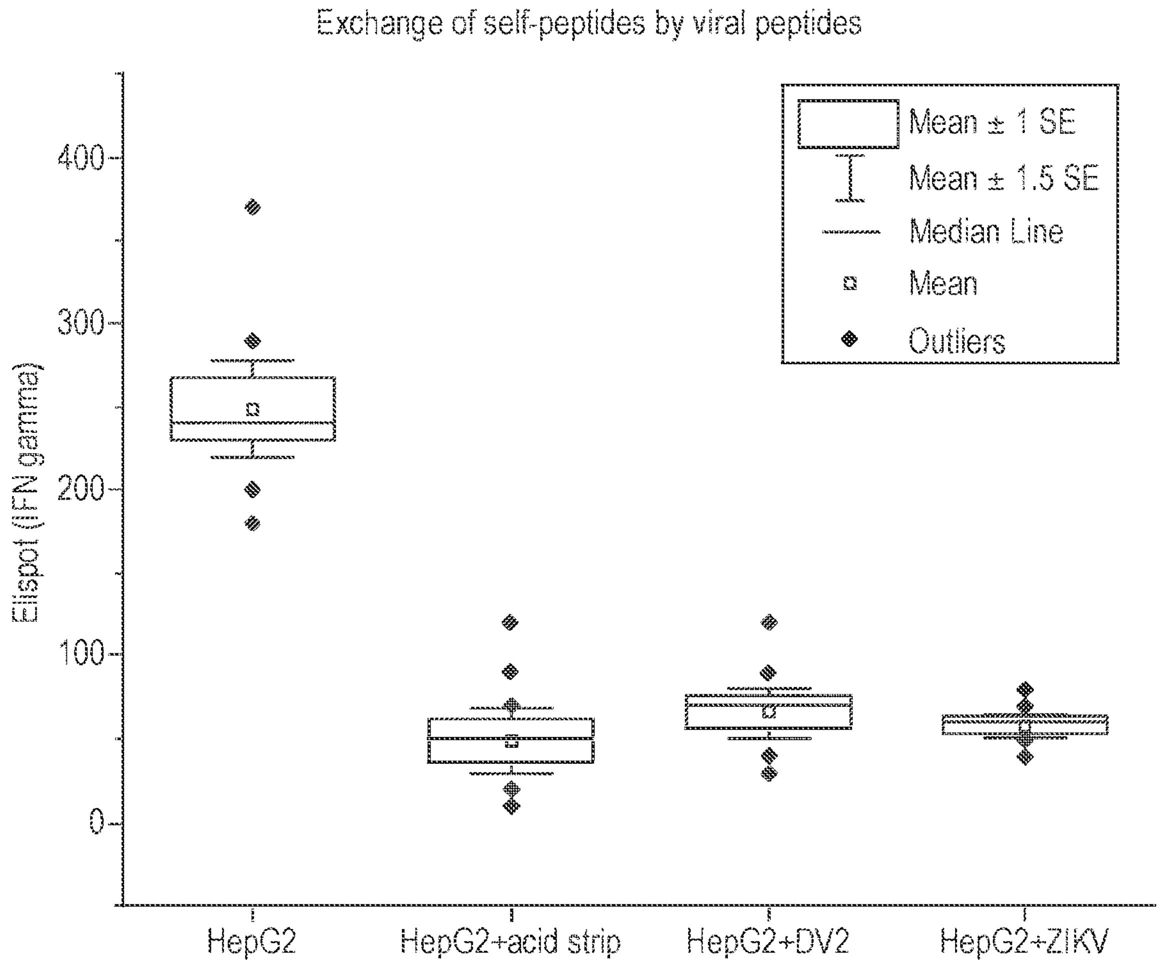
FIG. 5: Transgenic A2 mice were immunized with 200 ng of NP-Dengue peptides. The spleen cells were isolated and then exposed to either Zika or Dengue infected cells.
Figure 6:
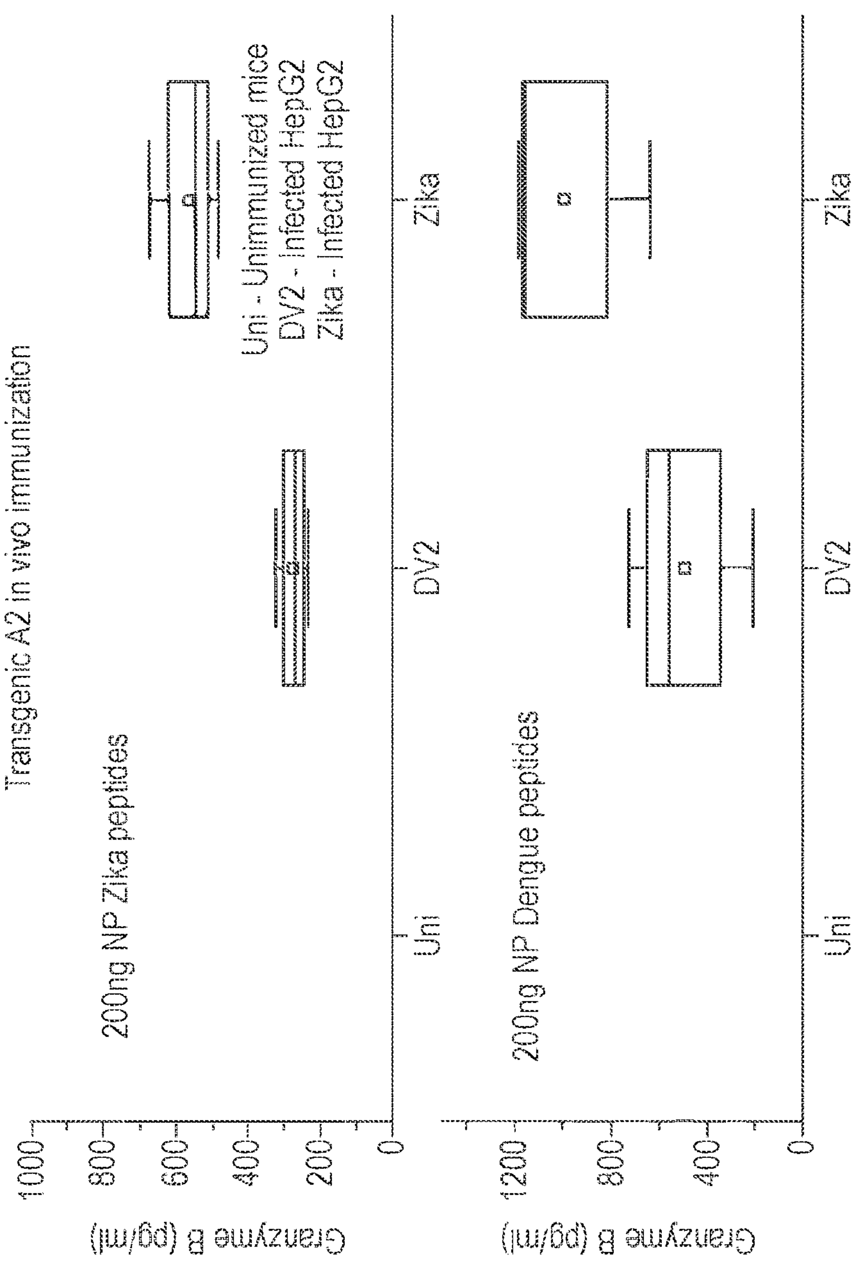
FIG. 6: Transgenic A2 mice were immunized with 200 ng of NP-Dengue peptides. The spleen cells were isolated and then exposed to either Zika or Dengue infected cells. Infection of the HepG2 cells with flaviviruses displaces the self-peptides and results in exposure of the viral derived peptides on the cell surface as shown in FIG. 6.

Transgenic A2 mice were also immunized with 200 ng of NP-Dengue peptides. The spleen cells were isolated and then exposed to either Zika or Dengue infected cells. FIG. 5 shows that HepG2 target cells contain peptide class I targets that are able to simulate spleen cells from transgenic A2 mice. Acid stripping of the peptides makes the cells non-response. Similarly, infection of the HepG2 cells with flaviviruses displaces the self-peptides and results in exposure of the viral derived peptides on the cell surface as shown in FIG. 6. FIG. 6 shows that spleen cells from unimmunized mice do not respond to dengue or zika infected cells. In contrast A2 mice immunized with NP-Dengue or NP-Zika peptides are able to kill both Dengue or Zika infected HepG2 cells.

2. Vaccine Platform

The vaccine platform described herein derives from the combination of two technologies, these being a library of experimentally validated cross-reactive viral peptides and a gold nanoparticle carrier system. The present inventors have generated library of experimentally validated cross-reactive viral MHC Class-I peptides that are involved in the T-cell response to a range of viral indications. The gold nanoparticle technology can improve the in vivo immunogencity of the peptides to help ensure that their administration produces a T-cell response sufficient for an effective clinical vaccine. By attaching the viral peptides and various carbohydrates to a gold nano core (typically <1.6 nm nanometre) a vaccine construct that is immunogenic and able to deliver the viral peptides inducing an immune response and generating antigen specific CD8 T cells can be produced. Successfully combined, the peptide library and the gold nanoparticle carrier technology will produce a vaccine capable of delivering the right peptides, to APCs (Antigen Presenting Cells), and produce a strong T-cell vaccine response.

A vaccine generated using this technology has the following properties:

a. Using a combination of conserved, internal T-cell inducing viral epitopes common to all Dengue a single vaccine 2 dose regimen could induce life-long immune protection against all existing and newly arising strains. By selecting the right combination of peptides that contain epitopes with certain HLA supertypes (HLA-A2/A24/A3), over 95% of the population could be effectively immunized.

b. The synthetic nature of the active immunogen/vaccine means the vaccine product would be highly stable at ambient temperatures and have a long shelf-life (>2 years). Vaccines would not require a cold chain, reducing the cost and risk of getting the vaccine to the user base in a functional condition and/or long-term stockpiling. Stability of a peptide product using the same GNP delivery system has shown stability of at >2 years. The GNP also protects attached peptides from proteolytic degradation c. Although the vaccines would be suited to the traditional parental routes of administration, the small size and stability of the vaccines means they would also be suited to delivery via the dermis (skin) using microneedle patches. The simplicity of this method of administration means specialist skills are not required for immunisation. This would allow the users to have an initial dose from a local vaccine provider/distributor, but any follow up doses could be provided to take home by the user for self-administration. This method may well improve compliance as the need to travel is reduced.

d. Another advantage of dermal delivery is that since the vaccine is presented directly to antigen presenting cells (APCs) within the dermis/epidermis, a much lower dose is required compared to other methods of administration which is favourable from both a safety and health economic perspective. The APCs which take up the viral peptides receptors will rapidly move to local/distant lymph nodes where a strong and long lasting the immune response will be initiated.

e. The production process is fast, inexpensive and highly scalable. There are in principle no limitations on production capacity, nor any known bottlenecks in the supply of raw materials, as all components can be synthesised using widely available equipment. GNP-peptide products have been successfully manufactured to GMP quality. Once the process is fully developed, manufacturing cost is estimated to be $0.1064 per dose with a current manufacturing capacity greater than 10 million doses per year. This capacity could be significantly higher with expanded facilities and multiple manufacturing sites.

f. Vaccines using this platform are expected to exhibit an excellent safety profile. This is due to the vaccines not requiring a live virus or attenuated viruses as components, nor requiring potentially toxic chemical adjuvants to be effective. The GNP carrier technology has already been shown to be safe in phase 1 and 2 clinical trials, including an insulin delivery system (Swiss Medic reference 2011 DR1183) and a type-1 Diabetes vaccine (Clinical trials.gov Reference: NCT02837094).

The invention claimed is:

1. A vaccine composition comprising a conjugate, the conjugate comprising a flavivirus peptide attached to a gold nanoparticle, wherein:

(i) the flavivirus peptide is 8 to 30 amino acids in length, and comprises a CD8+ T cell epitope comprising the amino acid sequence set forth in SEQ ID NO: 15 or SEQ ID NO: 18, or a variant thereof which differs from SEQ ID NO: 15 or SEQ ID NO: 18 by one amino acid substitution, deletion or insertion; and (ii) the gold nanoparticle is coated with galactose and/or GlcNAc.

2. The vaccine composition of claim 1, wherein the gold nanoparticle is coated with alpha-galactose and/or beta-GlcNAc.

3. The vaccine composition of claim 1, wherein the gold nanoparticle is coated with galactose and GlcNAc.

4. The vaccine composition of claim 1, wherein the flavivirus peptide is attached to the nanoparticle by a linker.

5. The vaccine composition of claim 4, wherein the linker has the structure:

$$—S—(CH_2)_2—CONH\text{-}AAY\text{-}$$

wherein the S is attached to the nanoparticle and AAY is a peptide joined to the N-terminus of the flavivirus peptide.

6. The vaccine composition of claim 1, wherein the variant differs from SEQ ID NO: 15 or SEQ ID NO: 18 by one conservative amino acid substitution.

7. The vaccine composition of claim 1, wherein the flavivirus peptide comprises the T cell epitope set forth in SEQ ID NO: 15.

8. The vaccine composition of claim 1, wherein the flavivirus peptide comprises the T cell epitope set forth in SEQ ID NO: 18.

9. The vaccine composition of claim 1, comprising a first conjugate and a second conjugate, each comprising a flavivirus peptide attached to a gold nanoparticle, wherein each flavivirus peptide is 8 to 30 amino acids in length, the gold nanoparticle is coated with galactose and GlcNAc and:

(i) the first conjugate comprises a flavivirus peptide comprising a first CD8+ T cell epitope comprising the amino acid sequence set forth in SEQ ID NO: 15 or SEQ ID NO: 18, or a variant thereof which differs from SEQ ID NO: 15 or SEQ ID NO: 18 by one amino acid substitution, deletion or insertion; and (ii) the second conjugate comprises a flavivirus peptide comprising a second CD8+ T cell epitope comprising the amino acid sequence set forth in any one of SEQ ID NOs: 1 to 23, or a variant thereof which differs from any one of SEQ ID NOs: 1 to 23 by one amino acid substitution, deletion or insertion;

wherein the first and second CD8+ T cell epitopes are different.

10. The vaccine composition of claim 9, comprising:

(i) a conjugate comprising SEQ ID NO: 15 or a variant thereof;

(ii) a conjugate comprising SEQ ID NO: 16 or a variant thereof;

(iii) a conjugate comprising SEQ ID NO: 17 or a variant thereof;

(iv) a conjugate comprising SEQ ID NO: 18 or a variant thereof;

(v) a conjugate comprising SEQ ID NO: 19 or a variant thereof;

(vi) a conjugate comprising SEQ ID NO: 20 or a variant thereof;

(vii) a conjugate comprising SEQ ID NO: 21 or a variant thereof;

(viii) a conjugate comprising SEQ ID NO: 22 or a variant thereof; and (ix) a conjugate comprising SEQ ID NO: 23 or a variant thereof;

wherein said variants differ from each of SEQ ID NOs: 15 to 23 by one amino acid substitution, deletion or insertion.

11. The vaccine composition of claim 10, comprising:

(i) a conjugate comprising SEQ ID NO: 15;

(ii) a conjugate comprising SEQ ID NO: 16;

(iii) a conjugate comprising SEQ ID NO: 17;

(iv) a conjugate comprising SEQ ID NO: 18;

(v) a conjugate comprising SEQ ID NO: 19;

(vi) a conjugate comprising SEQ ID NO: 20;

(vii) a conjugate comprising SEQ ID NO: 21;

(viii) a conjugate comprising SEQ ID NO: 22; and (ix) a conjugate comprising SEQ ID NO: 23.

12. The vaccine composition of claim 1, further comprising a pharmaceutically acceptable diluent, carrier or excipient.

13. A method of treating or preventing a flavivirus infection in a subject, comprising administering the vaccine composition of claim 1 to an individual infected with, or at risk of being infected with, a flavivirus.

14. The method of claim 13, wherein the method is for preventing a flavivirus infection in a subject, and the individual is at risk of being infected with a flavivirus.

15. The method of claim 13, wherein the flavivirus infection is a Zika virus infection, West Nile virus infection, dengue virus infection, yellow fever virus infection, and/or Japanese encephalitis virus infection.

16. The method of claim 15, wherein the flavivirus infection is a dengue virus infection.

17. The method of claim 13, wherein the method comprises intradermal or transdermal administration of the vaccine composition to the individual.

18. The vaccine composition of claim 2, wherein the gold nanoparticle is coated with alpha-galactose and beta-GlcNAc.

19. A method of stimulating an immune response in an individual, comprising administering to the individual the vaccine composition of claim 1.

20. The method of claim 19, wherein the method comprises intradermal or transdermal administration of the vaccine composition to the individual.

* * * * *

SEQUENCE LISTING

```
Sequence total quantity: 25
SEQ ID NO: 1            moltype = AA  length = 10
FEATURE                 Location/Qualifiers
source                  1..10
                        mol_type = protein
                        organism = Dengue virus
SEQUENCE: 1
IAVAVSSAIL                                                     10

SEQ ID NO: 2            moltype = AA  length = 11
FEATURE                 Location/Qualifiers
source                  1..11
                        mol_type = protein
                        organism = Dengue virus
```

-continued

```
SEQUENCE: 2
PMAAVGLLIV S                                                      11

SEQ ID NO: 3            moltype = AA  length = 10
FEATURE                 Location/Qualifiers
source                  1..10
                        mol_type = protein
                        organism = Dengue virus
SEQUENCE: 3
WVTDHSGKTV                                                        10

SEQ ID NO: 4            moltype = AA  length = 10
FEATURE                 Location/Qualifiers
source                  1..10
                        mol_type = protein
                        organism = Dengue virus
SEQUENCE: 4
WVTDHSGKTV                                                        10

SEQ ID NO: 5            moltype = AA  length = 10
FEATURE                 Location/Qualifiers
source                  1..10
                        mol_type = protein
                        organism = Zika virus
SEQUENCE: 5
IMLLGLLGTV                                                        10

SEQ ID NO: 6            moltype = AA  length = 13
FEATURE                 Location/Qualifiers
source                  1..13
                        mol_type = protein
                        organism = Zika virus
SEQUENCE: 6
ALGLTAVRLV DPI                                                    13

SEQ ID NO: 7            moltype = AA  length = 15
FEATURE                 Location/Qualifiers
source                  1..15
                        mol_type = protein
                        organism = Zika virus
SEQUENCE: 7
DESRAKVEVT PNSPR                                                  15

SEQ ID NO: 8            moltype = AA  length = 10
FEATURE                 Location/Qualifiers
source                  1..10
                        mol_type = protein
                        organism = Zika virus
SEQUENCE: 8
DPAVIGTAVK                                                        10

SEQ ID NO: 9            moltype = AA  length = 11
FEATURE                 Location/Qualifiers
source                  1..11
                        mol_type = protein
                        organism = Zika virus
SEQUENCE: 9
WPPSEVLTAV G                                                      11

SEQ ID NO: 10           moltype = AA  length = 11
FEATURE                 Location/Qualifiers
source                  1..11
                        mol_type = protein
                        organism = Zika virus
SEQUENCE: 10
DIGAVALDYP A                                                      11

SEQ ID NO: 11           moltype = AA  length = 10
FEATURE                 Location/Qualifiers
source                  1..10
                        mol_type = protein
                        organism = Dengue virus
SEQUENCE: 11
EWEKRIAEAI                                                        10

SEQ ID NO: 12           moltype = AA  length = 11
FEATURE                 Location/Qualifiers
source                  1..11
                        mol_type = protein
                        organism = Dengue virus
```

```
SEQUENCE: 12
FILLSMVGIA A                                                      11

SEQ ID NO: 13           moltype = AA  length = 10
FEATURE                 Location/Qualifiers
source                  1..10
                        mol_type = protein
                        organism = Dengue virus
SEQUENCE: 13
FLMCKTTDMV                                                        10

SEQ ID NO: 14           moltype = AA  length = 10
FEATURE                 Location/Qualifiers
source                  1..10
                        mol_type = protein
                        organism = Dengue virus
SEQUENCE: 14
LQAVMAVPDT                                                        10

SEQ ID NO: 15           moltype = AA  length = 9
FEATURE                 Location/Qualifiers
source                  1..9
                        mol_type = protein
                        organism = Dengue virus
SEQUENCE: 15
KLAEAIFKL                                                         9

SEQ ID NO: 16           moltype = AA  length = 10
FEATURE                 Location/Qualifiers
source                  1..10
                        mol_type = protein
                        organism = Dengue virus
SEQUENCE: 16
AMLSIPNAII                                                        10

SEQ ID NO: 17           moltype = AA  length = 9
FEATURE                 Location/Qualifiers
source                  1..9
                        mol_type = protein
                        organism = Dengue virus
SEQUENCE: 17
LLCVPNIMI                                                         9

SEQ ID NO: 18           moltype = AA  length = 9
FEATURE                 Location/Qualifiers
source                  1..9
                        mol_type = protein
                        organism = Dengue virus
SEQUENCE: 18
TITEEIAVQ                                                         9

SEQ ID NO: 19           moltype = AA  length = 9
FEATURE                 Location/Qualifiers
source                  1..9
                        mol_type = protein
                        organism = Dengue virus
SEQUENCE: 19
LVMKDGRKL                                                         9

SEQ ID NO: 20           moltype = AA  length = 10
FEATURE                 Location/Qualifiers
source                  1..10
                        mol_type = protein
                        organism = Dengue virus
SEQUENCE: 20
LLGQGPMKLV                                                        10

SEQ ID NO: 21           moltype = AA  length = 9
FEATURE                 Location/Qualifiers
source                  1..9
                        mol_type = protein
                        organism = Dengue virus
SEQUENCE: 21
LMRNKGIGK                                                         9
```

-continued

```
SEQ ID NO: 22          moltype = AA  length = 9
FEATURE                Location/Qualifiers
source                 1..9
                       mol_type = protein
                       organism = Dengue virus
SEQUENCE: 22
SPARLASAI                                                    9

SEQ ID NO: 23          moltype = AA  length = 14
FEATURE                Location/Qualifiers
source                 1..14
                       mol_type = protein
                       organism = unidentified
                       note = Flavivirus
SEQUENCE: 23
APTRVVAAEM EEAL                                              14

SEQ ID NO: 24          moltype = AA  length = 18
FEATURE                Location/Qualifiers
source                 1..18
                       mol_type = protein
                       organism = Clostridium tetani
SEQUENCE: 24
FKLQTMVKLF NRIKNNVA                                          18

SEQ ID NO: 25          moltype = AA  length = 19
FEATURE                Location/Qualifiers
source                 1..19
                       mol_type = protein
                       organism = Clostridium tetani
SEQUENCE: 25
LQTMVKLFNR IKNNVAGGC                                         19
```